United States Patent
Vo-Dinh et al.

(10) Patent No.: US 12,354,261 B2
(45) Date of Patent: Jul. 8, 2025

(54) SMART PHONE PLATFORMS FOR MOBILE HEALTH

(71) Applicant: Duke University, Durham, NC (US)

(72) Inventors: Tuan Vo-Dinh, Durham, NC (US); Tushar Krishnan, Durham, NC (US); Hsin-Neng Wang, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 413 days.

(21) Appl. No.: 18/060,465

(22) Filed: Nov. 30, 2022

(65) Prior Publication Data

US 2023/0169656 A1 Jun. 1, 2023

Related U.S. Application Data

(60) Provisional application No. 63/284,096, filed on Nov. 30, 2021.

(51) Int. Cl.
| | |
|---|---|
| *G06T 7/00* | (2017.01) |
| *G06V 10/25* | (2022.01) |
| *G06V 10/56* | (2022.01) |
| *G16H 30/40* | (2018.01) |
| *G16H 50/20* | (2018.01) |

(52) U.S. Cl.
CPC ............ *G06T 7/0012* (2013.01); *G06V 10/25* (2022.01); *G06V 10/56* (2022.01); *G16H 30/40* (2018.01); *G16H 50/20* (2018.01); *G06T 2207/30204* (2013.01)

(58) Field of Classification Search
CPC ........ G06T 7/0012; G06T 2207/30204; G16H 50/20; G16H 30/40; G06V 10/25; G06V 10/56
See application file for complete search history.

(56) References Cited

U.S. PATENT DOCUMENTS

| | | | | |
|---|---|---|---|---|
| 2018/0348136 | A1* | 12/2018 | Treado ................... | G01N 21/65 |
| 2021/0270722 | A1* | 9/2021 | Chou ..................... | G16H 30/40 |

OTHER PUBLICATIONS

Wang, Jia-Wei, et al., "MiR156-Regulated SPL Transcription Factors Define an Endogenous Flowering Pathway in *Arabidopsis thaliana*", Cell, 2009, pp. 738-749, vol. 138 (4), https://doi.org/10.1016/j.cell.2009.06.014.

(Continued)

*Primary Examiner* — Quang N Vo
(74) *Attorney, Agent, or Firm* — NK Patent Law

(57) ABSTRACT

A diagnostic mobile health system for detecting biomarkers comprises an electronic device including an image sensor configured to capture image data, a sample housing configured to removably attach to the electronic device, and a computing device including at least one processor. The sample housing includes a slot to receive a sample container. The sample container received in the slot is positioned to allow the image sensor to capture image data for the sample when the sample housing is attached to the electronic device. The processor is configured for receiving, from the electronic device, image data for the sample that is captured by the image sensor of the electronic device when the sample container containing the sample is received by the sample housing attached to the electronic device and detecting at least one biomarker for the sample based on the received image data.

19 Claims, 26 Drawing Sheets

(56) References Cited

OTHER PUBLICATIONS

Wang, Hsin-Neng, et al., "Plasmonic coupling interference (PCI) nanoprobes for nucleic acid detection", Small, pp. 3067-3074, vol. 7(21), doi:10.1002/smll.201101380.

Wang, Wei, et al., "Label-Free MicroRNA Detection Based on Fluorescence Quenching of Gold Nanoparticles with a Competitive Hybridization", Analytical Chemistry, 2015, pp. 10822-10829, vol. 87 (21), https://doi.org/10.1021/acs.analchem.5b01930.

Wang, Feiyang, et al., "Smartphone Readable Colorimetric Sensing Platform for Rapid Multiple Protein Detection", Analyst, 2017, pp. 3177-3182, vol. 142 (17), https://doi.org/10.1039/C7AN00990A.

Wang, Hsin-Neng, et al., "Direct and Label-Free Detection of MicroRNA Cancer Biomarkers Using SERS-Based Plasmonic Coupling Interference (PCI) Nanoprobes", Journal of Physical Chemistry, 2019, pp. 10245-10251, vol. 123 (48), https://doi.org/10.1021/acs.jpcb.9b06804.

Wang, Hsi-Neng, et al., "Plasmonic Coupling Interference (PCI), Nanoprobes for Nucleic Acid Detection", Small, 2011, pp. 3067-3074, vol. 7, No. 11.

Weber, Jessica A., et al., "The MicroRNA Spectrum in 12 Body Fluids", Clinical Chemistry, 2010, pp. 1733 1741, vol. 56 (11), https://doi.org/10.1373/clinchem.2010.147405.

Weiland, Matthew, et al., "Small RNAs Have a Large Impact: Circulating MicroRNAs as Biomarkers for Human Diseases", RNA Biology, 2012, pp. 850-859, vol. 9 (6), https://doi.org/10.4161/ma.20378.

Wu, Ye E., et al., "Genome-Wide, Integrative Analysis Implicates MicroRNA Dysregulation in Autism Spectrum Disorder", Nat Neurosci, 2016, pp. 1463-1476, vol. 19 (11), https://doi.org/10.1038/nn.4373.

Yetisen, Ali K., et al., "A Smartphone Algorithm with Inter-Phone Repeatability for the Analysis of Colorimetric Tests", Sensors and Actuators B: Chemical, 2014, pp. 156-160, vol. C (196), https://doi.org/10.1016/j.snb.2014.01.077.

Zhang, Diming, et al., "Biosensors and Bioelectronics on Smartphone for Portable Biochemical Detection", Biosensors and Bioelectronics, 2016, pp. 273-284, vol. 75, https://doi.org/10.1016/j.bios.2015.08.037.

Basak, I., et al., "microRNAs as neuroregulators, biomarkers and therapeutic agents in neurodegenerative diseases", Cellular and Molecular Life Sciences, 2016, pp. 811-827, vol. 73 (4), https://doi.org/10.1007/s00018-015-2093-x.

Chan, Ho Nam, et al., "Simple, Cost-Effective 3D Printed Microfluidic Components for Disposable, Point-of-Care Colorimetric Analysis", ACS Sens. 2016, pp. 227-234, vol. 1 (3), https://doi.org/10.1021/acssensors.5b00100.

Chen, Yuan, et al., "H. A Smartphone Colorimetric Reader Integrated with an Ambient Light Sensor and a 3D Printed Attachment for On-Site Detection of Zearalenone", Anal Bioanal Chem, 2017, pp. 6567-6574, vol. 409 (28), https://doi.org/10.1007/s00216-017-0605-2.

Choi, Seoyeon, et al., "Real-Time Measurement of Human Salivary Cortisol for the Assessment of Psychological Stress Using a Smartphone", Sensing and Bio-Sensing Research, 2014, pp. 8-11, vol. 2, https://doi.org/10.1016/j.sbsr.2014.08.001.

Crawford, Bridget M., et al., "Plasmonic Nanoprobes for in Vivo Multimodal Sensing and Bioimaging of MicroRNA within Plants", ACS Applied Materials and Interfaces, 2019, pp. 7743-7754, vol. 11 (8), https://doi.org/10.1021/acsami.8b19977.

Degliangeli, Federica, et al., "Nanotechnology-Based Strategies for the Detection and Quantification of MicroRNA", Chemistry—A European Journal, 2014, pp. 9476-9492, vol. 20 (31), https://doi.org/10.1002/chem.201402649.

Doria, Goncalo, et al., "Noble Metal Nanoparticles for Biosensing Applications", Sensors, 2012, pp. 1657-1687, vol. 12 (2), https://doi.org/10.3390/s120201657.

Duan, Junling, et al., "Facile Colorimetric Detection of Hg2+ Based on Anti-Aggregation of Silver Nanoparticles", Biosensors and Bioelectronics, 2014, pp. 139-142, vol. 57, https://doi.org/10.1016/j.bios.2014.02.007.

Dutta, Sibasish, et al., "Protein, Enzyme and Carbohydrate Quantification Using Smartphone through Colorimetric Digitization Technique", Journal of Biophotonics, 2017, pp. 623-633, vol. 10 (5), https://doi.org/10.1002/ibio.201500329.

Guah, Claudiane, et al., "Circulating MicroRNAs as Novel Biomarkers for Diabetes Mellitus", Nature Reviews/ Endocrinology, 2013, pp. 513-521, vol. 9 (9), https://doi.org/10.1038/nrendo.2013.86.

Hayes, Josie, et al., MicroRNAs in Cancer: Biomarkers, Functions and Therapy, Trends in Molecular Medicine, Aug. 2014, pp. 460-469, vol. 20 (8), https://doi.org/10.1016/j.molmed.2014.06.005.

He, Liin, et al., "MicroRNAs: Small RNAs with a Big Role in Gene Regulation", Nature Reviews, Genetics, 2004, pp. 522-531, vol. 5 (7),https://doi.org/10.1038/nrg1379.

Hernandez-Neuta, I., et al., "Smartphone-based clinical diagnostics: towards democratization of evidence-based health care", Journal of Internal Medicine, 2019, pp. 19-39, vol. 285(1), doi:10.1111/joim.12820.

Hicks, Steven D., et al., "A Comparative Review of MicroRNA Expression Patterns in Autism Spectrum Disorder", Frontiers in Psychiatry, 2016, pp. 1-10, vol. 7, Article 176, https://doi.org/10.3389/fpsyt.2016.00176.

Hong, Jong II, et al., "Development of the Smartphone-Based Colorimetry for Multi-Analyte Sensing Arrays", Lab on a Chip, 2014, pp. 1725-1732, vol. 14 (10), https://doi.org/10.1039/c3lc51451j.

Iorio, Marilena V., et al., "MicroRNA Dysregulation in Cancer: Diagnostics, Monitoring and Therapeutics. A Comprehensive Review", EMBO Molecular Medicine, 2012, pp. 143-159, vol. 4 (3), https://doi.org/10.1002/emmm.201100209.

Jain, Prashant K., et al., "Plasmonic Coupling in Noble Metal Nanostructures", Chemical Physics Letters, 2010, pp. 153-164, vol. 487 (4), https://doi.org/10.1016/j.cplett.2010.01.062.

Johnson, Blake N., et al., "Biosensor-Based MicroRNA Detection: Techniques, Design, Performance, and Challenges", Analyst, Minireview, 2014, pp. 1576-1588, vol. 139 (7), https://doi.org/10.1039/C3AN01677C.

Jung, Youngkee, et al., "Smartphone-Based Colorimetric Analysis for Detection of Saliva Alcohol Concentration", Applied Optics, Nov. 1, 2015, pp. 9183-9189, vol. 54 (31), https://doi.org/10.1364/AO.54.009183.

Kanchi, Suvardhan, et al., "Smartphone Based Bioanalytical and Diagnosis Applications: A Review", Biosensors and Bioelectronics, 2018, pp. 136-149, vol. 102, https://doi.org/10.1016/j.bios.2017.11.021.

Kilic, Tugba, et al., "MicroRNA Biosensors: Opportunities and Challenges among Conventional and Commercially Available Techniques", Biosensors and Bioelectronics, 2018, pp. 525-546, vol. 99, https://doi.org/10.1016/j.bios.2017.08.007.

Kim, Sang C., et al., "A Smartphone-Based Optical Platform for Colorimetric Analysis of Microfluidic Device", Sensors and Actuators B: Chemical, 2017, pp. 52-59, vol. C (239), https://doi.org/10.1016/j.snb.2016.07.159.

Kneipp, Katrin, et al., "Surface-enhanced Raman scattering and biophysics", Journal of Physics: Condensed Matter, 2002, pp. R597-R624, vol. 14, PII:S0953-8984(02)21355-7.

Krichevsky, Anna M., et al., "MiR-21: A Small Multi-Faceted RNA", Journal of Cellular and Molecular Medicine, 2009, pp. 39-53, vol. 13 (1), https://doi.org/10.1111/j.1582-4934.2008.00556.x.

Kwon, L., et al., "Medical diagnostics with mobile devices: Comparison of intrinsic and extrinsic sensing", Biotechnology Advances, 2016, pp. 291-304, vol. 34(3), doi:10.1016/j.biotechadv.2016.02.010.

Lee, Seoho, et al., "A Smartphone Platform for the Quantification of Vitamin D Levels", Lab on a Chip, 2014, pp. 1437-1442, vol. 14 (8), https://doi.org/10.1039/c3lc51375k.

Liu, Yuanjian, et al., "Colorimetric Detection of Influenza A Virus Using Antibody-Functionalized Gold Nanoparticles", Analyst, 2015, pp. 3989-3995, vol. 140 (12), https://doi.org/10.1039/C5AN00407A.

(56) References Cited

OTHER PUBLICATIONS

Lopez-Ruiz, Nuria, et al., "Smartphone-Based Simultaneous PH and Nitrite Colorimetric Determination for Paper Microfluidic Devices", Analytical Chemistry, 2014, pp. 9554-9562, vol. 86 (19), https://doi.org/10.1021/ac5019205.

Lu, Jun, et al., "MicroRNA Expression Profiles Classify Human Cancers", Nature, 2005, pp. 834-838, vol. 435 (7043), https://doi.org/10.1038/nature03702.

Mancuso, Matthew, et al., Detection of Kaposi's Sarcoma Associated Herpesvirus Nucleic Acids Using a Smartphone Accessory, Lab on a Chip, 2014, pp. 3809-3816, vol. 14 (19), https://doi.org/10.1039/C4LC00517A.

Miao, Jie, et al., "A Plasmonic Colorimetric Strategy for Visual MiRNA Detection Based on Hybridization Chain Reaction", Scientific Reports, 2016, pp. 1-7, vol. 6:32219, https://doi.org/10.1038/srep32219.

Mouillet-Richard, Sophie, et al., "MicroRNAs and Depression", Neurobiology of Disease, 2012, pp. 272-278, vol. 46 (2), https://doi.org/10.1016/j.nbd.2011.12.035.

Nie, Huaijun, et al., "A Colorimetric and Smartphone Readable Method for Uracil-DNA Glycosylase Detection Based on the Target-Triggered Formation of G-Quadruplex", Analyst, 2015, pp. 2771-2777, vol. 140 (8), https://doi.org/10.1039/c4an02339k.

Oncescu, Vlad, et al., "Smartphone Based Health Accessory for Colorimetric Detection of Biomarkers in Sweat and Saliva", Lab on a Chip, 2013, pp. 3232-3238, vol. 13 (16), https://doi.org/10.1039/c3lc50431j.

Oncescu, Vlad, et al., "Cholesterol Testing on a Smartphone", Lab on a Chip, 2014, pp. 759-763, vol. 14 (4), https://doi.org/10.1039/C3LC51194D.

Priye, Aashish, et al., "Lab-on-a-Drone: Toward Pinpoint Deployment of Smartphone-Enabled Nucleic Acid-Based Diagnostics for Mobile Health Care", Analytical Chemistry, 2016, pp. 4651-4660, vol. 88 (9), https://doi.org/10.1021/acs.analchem.5b04153.

Hunt, R.W.G., et al., "Measuring Colour", Wiley-IS&T Series in Imaging Science and Technology, Fourth Edition, 2011, pp. 1-479, John Wiley & Sons.

Redell, John B., et al., "Human Traumatic Brain Injury Alters Plasma MicroRNA Levels", Journal of Neurotrauma, Dec. 2010, pp. 2147-2156, vol. 27 (12), https://doi.org/10.1089/neu.2010.1481.

Reid, Glen, et al., "Circulating MicroRNAs: Association with Disease and Potential Use as Biomarkers", Critical Reviews in Oncology Hematology, 2011, pp. 193-208, vol. 80 (2), https://doi.org/10.1016/j.critrevonc.2010.11.004.

Roda, Aldo, et al, "Smartphone-Based Biosensors: A Critical Review and Perspectives", Trends in Analytical Chemistry, 2016, pp. 317-325, vol. C (79), https://doi.org/10.1016/j.trac.2015.10.019.

Romaine, Simon P R., et al., "MicroRNAs in Cardiovascular Disease: An Introduction for Clinicians", Heart, 2015, pp. 921-928, vol. 101 (12), https://doi.org/10.1136/heartjnl-2013-305402.

Sabela, Myalowenkosi, et al., "A Review of Gold and Silver Nanoparticle-Based Colorimetric Sensing Assays", Advanced Engineering Materials, 2017, pp. 1-25, vol. 19 (12), 1700270. https://doi.org/10.1002/adem.201700270.

Selcuklu, S. Duygu, "MiR-21 as a Key Regulator of Oncogenic Processes", Biochemical Society Transactions, 2009, pp. 918-925, vol. 37, Part 4, https://doi.org/10.1042/BST0370918.

Su, Kaiqi, et al., "High-Sensitive and High-Efficient Biochemical Analysis Method Using a Bionic Electronic Eye in Combination with a Smartphone-Based Colorimetric Reader System", Sensors and Actuators, 2015, pp. 134-140, vol. B 216.

Ebner, Marc, "Color Constancy", IS&T Series in Imaging Science and Technology, John Wiley & Sons, 2007, p. 1-406.

Tian, Tian, et al., "A Review: MicroRNA Detection Methods", Organic and Biomolecular Chemistry, 2015, pp. 2226-2238, vol. 13 (8), https://doi.org/10.1039/c4ob02104e.

Vashist, Sandeep Kumar, "A Smartphone-Based Colorimetric Reader for Bioanalytical Applications Using the Screen-Based Bottom Illumination Provided by Gadgets", Biosensors and Bioelectronics, 2015, pp. 248-255, vol. 67, https://doi.org/10.1016/j.bios.2014.08.027.

Verma, Parmila, et al., "Circulating MicroRNAs: Potential and Emerging Biomarkers for Diagnosis of Human Infectious Diseases", Frontiers in Microbiology, Aug. 15, 2016, pp. 1-7, https://doi.org/10.3389/fmicb.2016.01274.

Vo-Dinh, Tuan, "Surface-enhanced Raman spectroscopy for trace organic analysis", American Chemical Society, Aug. 1984, pp. 1667-1670, vol. 56.

Wang, Hsin-Neng, et al., "Plasmonic Coupling Interference (PCI) Nanoprobes for Nucleic Acid Detection", Nano Micro Small, Biosensors, 2011, pp. 3067-3074, vol. 7, No. 21.

\* cited by examiner

FIG. 1A
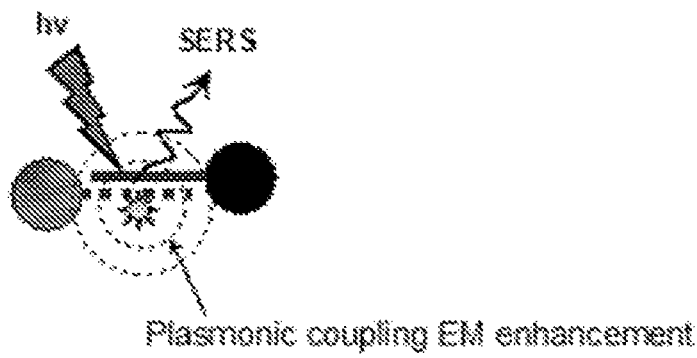
FIG. 1B
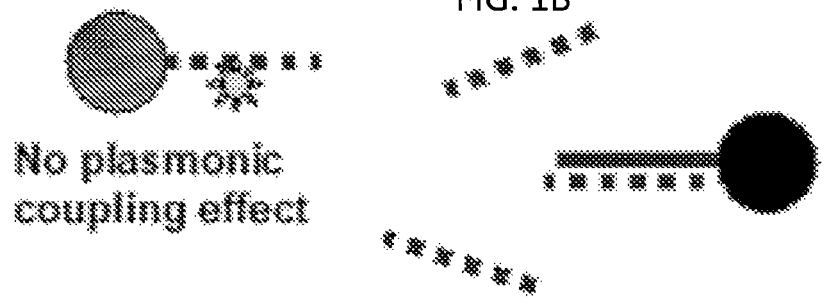
FIG. 1C
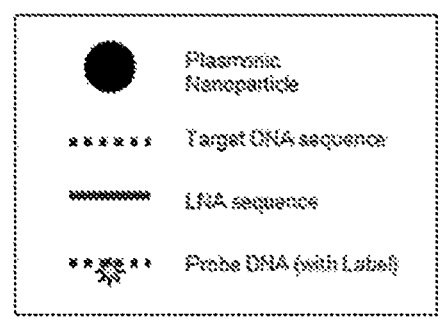

SMART PHONE PLATFORMS FOR MOBILE HEALTH

CROSS-REFERENCE TO RELATED APPLICATIONS

This application claims priority to U.S. Provisional Patent Application No. 63/284,096 filed on Nov. 30, 2021, which is incorporated by reference herein in its entirety.

BACKGROUND

There is a strong need to have practical devices and systems to rapidly detect and monitor diseases at the point of care, or in the field in remote areas far from clinical centers or in low-resource settings. Such devices can take advantage of the latest technologies of smartphones, which have experienced exponential growth worldwide, in order to achieve the potential of the next generation of mobile health.

One technology area that is currently underutilized is using nanoparticles for colorimetric analysis.

SUMMARY

The Summary is provided to introduce a selection of concepts that are further described below in the Detailed Description. This Summary is not intended to identify key or essential features of the claimed subject matter, nor is it intended to be used as an aid in limiting the scope of the claimed subject matter.

A system operable for the colorimetric detection and quantification of microRNA is described herein. In one embodiment, the system includes a remote device, a sample housing, and a software application designed for the detection of a disease biomarker (e.g., microRNA-21). The system, in another embodiment, further includes a nanoparticle-based assay. Advantageously, the system is designed to detect nanomolar concentrations of microRNAs. The software application is designed to provide accessible and affordable microRNA diagnostics for point-of-care and field applications in low-resource settings.

In a first aspect of the invention, a diagnostic mobile health device system for detecting biomarkers is provided. In a feature of this aspect, the diagnostic mobile health system comprises an electronic device including an image sensor configured to capture image data, a sample housing including a slot to receive a sample container that contains a sample, and a computing device including at least one processor designed to receive image data for the sample that is captured by the image sensor, and detect at least one biomarker based on the received image data.

In another aspect of the invention, a method for biomarker detection comprises receiving a sample via a sample housing removably attached to an electronic device, illuminating the sample with at least one light source of the electronic device, capturing image data of the sample via an image sensor of the electronic device, wherein the image data includes a red, green, and blue (RGB) value for each pixel of the captured image data, transmitting the captured image data to a computing device including a processor, averaging the RGB values using the processor of the computing device, normalizing the RGB values in comparison to RGB data for a template region of interest using the processor of the computing device, converting the normalized RGB values to color data and concentration data using the processor of the computing device, and detecting at least one biomarker for the sample based on the color data and the concentration data using the processor of the computing device.

In a further aspect of the invention, a mobile health device for detecting biomarkers comprises a sample housing including at least one slot, a cover, and a back plate that is removably attached to the mobile health device, an imaging sensor, and at least one processor. In a feature of this aspect, the at least one slot is operable to receive a sample container that contains a sample, the sample container received in the at least one slot is positioned to allow the image sensor to capture image data for the sample when the sample housing is attached to the mobile health device, the cover is positioned on a top side of the sample housing to block external light from entering the sample housing, and the at least one processor is configured for receiving from the image sensor, image data for the sample that is captured by the image sensor when the sample container containing the sample is received by the sample housing attached to mobile health device, and detecting at least one biomarker for the sample based on the received based on the image data.

In another aspect of the invention, an electronic device is configured for rapid colorimetric detection of microRNA. The electronic device consists of a remote device (e.g., a smartphone), a 3D printed accessory, and a custom-built dedicated mobile app. In a feature of this aspect, the electronic device is designed to detect a known disease biomarker, microRNA-21, using a nanoparticle-based assay, at nanomolar concentrations. Thus, the electronic device offers a practical colorimetric platform that has the potential to provide accessible and affordable miRNA diagnostics for point-of-care and field applications in low-resource settings.

BRIEF DESCRIPTION OF THE DRAWINGS

The accompanying Figures and Examples are provided by way of illustration and not by way of limitation. The foregoing aspects and other features of the disclosure are explained in the following description, taken in connection with the accompanying example figures (also "FIG.") relating to one or more embodiments, in which:

FIG. 1A illustrates a schematic diagram of Ag NPs functionalized with thiolated LNAs (capture NPs) or complementary DNA probes labeled with Cy3 Raman dye (report-NPs) according to one embodiment of the present invention.

FIG. 1B illustrates plasmonic coupling between adjacent NPs induced by the formation of LNA/DNA-probe duplexes according to one embodiment of the present invention.

FIG. 1C illustrates plasmonic coupling interference due to the formation of LNA-target DNA duplexes.

DETAILED DESCRIPTION

Figure 2A:
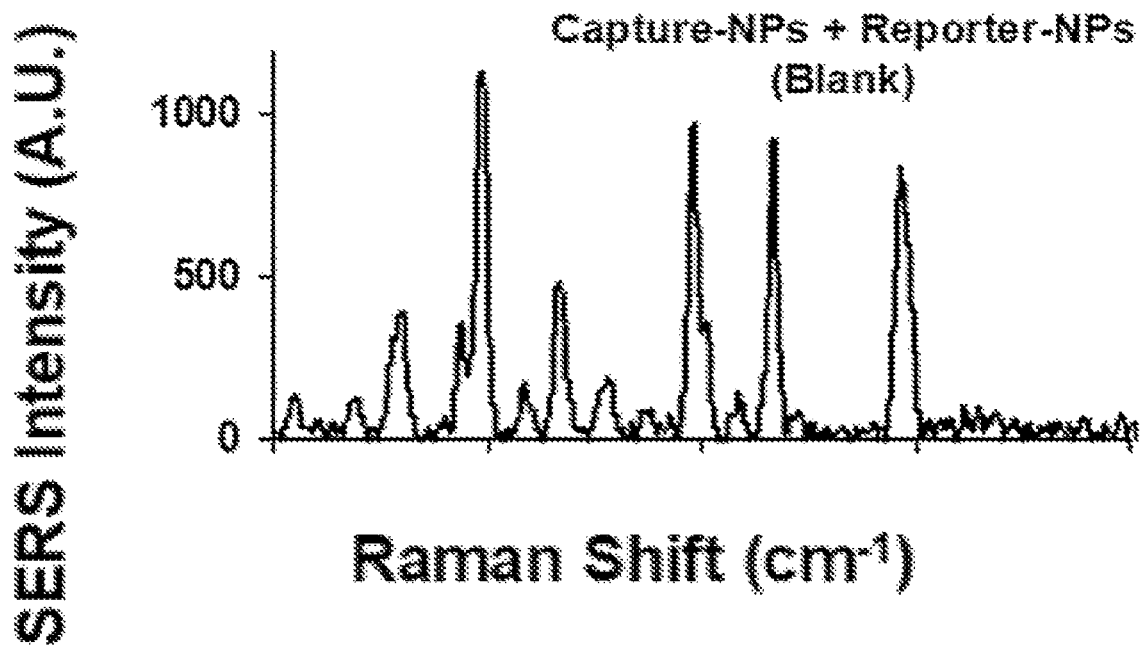
FIG. 2A illustrates a Service Enhanced Raman Scattering (SERS) spectra of Cy3 Raman peaks in the presence of both capture-NPs and reporter-NPs

For the purpose of promoting an understanding of the principles of the present disclosure, reference will now be made to embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e., at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder, or condition.

The term "effective amount" or "therapeutically effective amount" refers to an amount sufficient to affect beneficial or desirable biological and/or clinical results.

As used herein, the term "subject" and "patient" are used interchangeably and refer to both human and nonhuman animals. The term "nonhuman animals" includes all vertebrates, e.g., mammals and non-mammals, such as nonhuman primates, sheep, dog, cat, horse, cow, chickens, amphibians, reptiles, and the like. The methods and compositions disclosed herein can be used on a sample either in vitro (for example, on isolated cells or tissues) or in vivo in a subject (i.e., living organism, such as a patient). In some embodiments, the subject comprises a human who is undergoing a procedure using the systems and methods described herein.

Unless otherwise defined, all technical terms used herein have the same meaning as commonly understood by one of ordinary skill in the art to which this disclosure belongs.

With their widespread adoption across the globe, ease of use, and consistent software and hardware advancements, smartphones present an opportunity to redefine mobile health and diagnostics. Smartphone-based diagnostic tools can provide an inexpensive, compact, and portable alternative to traditional laboratory diagnostic instruments, which are bulky and costly, and generally require a peripheral computer to function. Mobile applications accessed through smartphones manage and automate much of the data acquisition and processing of smartphone-based diagnostic tools. A smartphone's internal sensor framework can be leveraged to acquire data, or a smartphone can be connected to external sensors. A common sensor used for diagnostic purposes is a smartphone's built-in camera. The smartphone camera has been used as an optical detector for microscopy imaging, and for the analysis of color-, fluorescence- and luminescence-based assays.

Smartphone-based colorimetric systems reported in literature have tested assays in solutions, via test strips or using microfluidic devices. Various biomolecules have been analyzed using such systems including proteins, nucleic acids, and biomarkers in blood, urine, saliva, and sweat, showing their capability as potential diagnostic tools. However, smartphone-based optical systems using ambient lighting during image data acquisition are affected by the inherent variability in the conditions between measurements. Various approaches to address this problem include normalization using reference color areas and enclosing the sample in a box/accessory to block outside light. The latter approach also tackles the concerns regarding relative movement between the smartphone and the sample since the accessory holds the samples in a fixed position relative to the camera lens. The accessories of these smartphone-based systems frequently contain various optical and electrical components that can make the systems more complex and less robust. There is a need for developing practical and rugged smartphone-based devices that can be efficiently deployed for field applications.

A diagnostic mobile health system for detecting biomarkers is described herein. The system comprises an electronic device including an image sensor configured to capture image data, a sample housing configured to removably attach to the electronic device, and a computing device including at least one processor. The sample housing includes a slot to receive a sample container that contains a sample. When the sample container is received in the slot, it is positioned to allow the image sensor of the electronic device to capture image data for the sample when the sample housing is attached to the electronic device. The at least one processor is configured for receiving, from the electronic device, image data for the sample that is captured by the image sensor of the electronic device when the sample container containing the sample is received by the sample housing attached to the electronic device; and detecting at least one biomarker for the sample based on the received image data.

The at least one biomarker can include microRNA. The detection of microRNAs is emerging as a clinically relevant tool for non-invasive detection of a wide variety of diseases ranging from cancers and cardiovascular illnesses to infectious diseases. Over the years, microRNA detection schemes have become accessible to clinicians but still require sophisticated and bulky laboratory equipment and trained personnel to operate. The exceptional computing ability and ease of use of modern smartphones coupled with field-transferable optical detection schemes can provide a useful and portable alternative to these laboratory systems.

MicroRNAs are small, non-coding RNAs of approximately 20-25 nucleotides in length that bind via hybridization to complementary sequences in the untranslated regions of target messenger RNA (mRNA), thereby allowing them to act as gene expression regulators post transcription. As miRNA levels affect mRNA translation and degradation, their dysregulation is often detected in various diseases, such as cancers. Recent studies have demonstrated that the expression profiles of miRNAs are dysregulated in many diseases, including cancer, cardiovascular illnesses, infectious diseases, diabetes, neurodegenerative diseases, autism, autoimmune disorders, traumatic brain injury, and depression. For these reasons, miRNAs have the potential to serve as useful biomarkers for the early detection of cancer and for predicting patient outcomes. Accurate and rapid detection and quantification of miRNA levels are, therefore, of considerable clinical significance.

Traditional approaches to miRNA detection include Northern blot, microarray, and quantitative reverse transcriptase (qRT)-PCR. These methods are often time-consuming, and laborious and require the use of expensive equipment. Recently, there has been a growing interest in developing alternate nanotechnology-based methods for miRNA detection. Biosensing strategies based on metal nanoparticles, such as gold and silver, have been widely studied due to their high sensitivity, low cost, and simple approach. In recent years, these strategies have been applied to some studies involving miRNA detection (e.g., a scheme to detect miRNA using the fluorescence quenching of gold nanoparticles; a colorimetric method for miRNA analysis based on hybridization chain reaction using silver nanoparticles). However, such systems are limited by their requirement of laboratory equipment for detection and analysis (e.g., spectrophotometer), making portability and point-of-care applications impractical.

The processor of the computing device of the mobile health system described herein is operable to detect the at least one biomarker using at least one of Raman scattering, luminescence detection, fluorescence detection, and/or phosphorescence detection. Moreover, when the sample includes a nanoparticle assay, the processor of the computing device is operable to quantify the at least one biomarker based on a color change of the sample using the received image data. With these features, the mobile health system is able to use the nano-network plasmonic couple interference (NPCI) principle to detect and diagnose diseases and/or other health conditions.

The NPCI principle is based on the interference of the plasmonics enhancement mechanisms of the electromagnetic field effect. There are two main sources of electromagnetic enhancement: (1) first, the laser electromagnetic field is enhanced due to the addition of a field caused by the polarization of the metal particle; and (2) in addition to the enhancement of the excitation laser field, there is also another enhancement due to the molecule radiating an amplified emission (luminescence, Raman, etc.) field, which further polarizes the metal particle, thereby acting as an antenna to further amplify the Raman/Luminescence signal. Electromagnetic enhancements are divided into two main classes: a) enhancements that occur only in the presence of a radiation field, and b) enhancements that occur even without a radiation field. The first class of enhancements is further divided into several processes. Plasma resonances on the substrate surfaces, also called surface plasmons, provide a major contribution to electromagnetic enhancement. An effective type of plasmonics-active substrate consists of nanostructured metal particles, protrusions, or rough surfaces of metallic materials. Incident light irradiating these surfaces excites conduction electrons in the metal and induces excitation of surface plasmons leading to Raman/Luminescence enhancement. At the plasmon frequency, the metal nanoparticles (or nanostructured roughness) become polarized, resulting in large field-induced polarizations and thus large local fields on the surface. These local fields increase the Luminescence/Raman emission intensity, which is proportional to the square of the applied field at the molecule. As a result, the effective electromagnetic field experienced by the analyte molecule on these surfaces is much larger than the actual applied field. This field decreases as 1/r3 away from the surface. Therefore, in the electromagnetic models, the luminescence/Raman-active analyte molecule is not required to be in contact with the metallic surface but can be located anywhere within the range of the enhanced local field, which can polarize this molecule.

Plasmonics-active metal nanoparticles exhibit strongly enhanced visible and near-infrared light absorption; several orders of magnitude more intense compared to conventional laser phototherapy agents. The use of plasmonic nanoparticles as highly enhanced photoabsorbing agents has thus introduced a much more selective and efficient phototherapy strategy. The tunability of the spectral properties of the metal nanoparticles and the biotargeting abilities of the plasmonic nanostructures make the NPCI method promising.

The operating principle of the NPCI detection strategy using functionalized Ag NPs is illustrated in FIGS. 1A-1C. In this approach, nanoparticles are coupled using the shortest separation distance in order to induce the strongest plasmonic coupling and a maximum Surface Enhanced Raman Scattering (SERS) enhancement of a Raman label located between two adjacent silver nanoparticles. Previous studies have shown that nanoparticles can be coupled using DNA oligonucleotides with over 8 bases. However, due to the thermal instability of short DNA-DNA duplexes, it is difficult to use DNA oligonucleotides shorter than 8 bases for assembling nanoparticles into a nano-network. To overcome this barrier, short locked nucleic acids (LNAs) with 7 bases were used in order to couple nanoparticles in a separation distance between 2 to 3 nm. It has been previously reported that LNAs can offer a high salt and thermal stability for coupling nanoparticles.

As shown in FIG. 1A, 30-nm-diameter Ag NPs are first functionalized with 0.5-μM thiolated LNAs with the sequence of 5'-dithiol-GGGCGGG-3' (referred to as capture-NPs) or the complementary DNA probes with the sequence of 3'-CCCGCCC-dithiol-5' (referred to as reporter-NPs). The DNA probes are internally labeled with a Raman dye, Cy3 as the signal reporters located in the middle of the probe DNA sequences. These functionalized NPs are then further conjugated with low molecular weight thiolated poly(ethylene glycol)s (HS-PEGs). It has been indicated that short PEGs can provide the Ag NPs stability in sodium phosphate buffer solution containing 100 mM NaCl. To displace the potential non-specifically adsorbed LNAs or DNAs, 6-Mercapto-1-hexanol (MCH) is used in the final step to passivate the silver surface.

FIG. 1B illustrates plasmonic coupling between adjacent NPs induced by the formation of LNA/DNA-probe duplexes which couple NPs in a short separation distance. Due to the same sequences of the reporter-probes and the target DNA, target DNA strands compete with reporter-NPs for binding to capture-NPs. To induce plasmonic coupling effect, capture-NPs and reporter-NPs are mixed in a volume ratio of 1:1 in order to form LNA-DNA duplexes. The mixture is allowed to react at room temperature in a 10-mM sodium phosphate buffer solution (pH 7.0) containing 50 mM NaCl and 2 to 5 mM $MgCl_2$. The duplex formation assembles nanoparticles into a three-dimensional nano-network of NPs having the Cy3 label located between adjacent NPs (FIG. 1B). In this situation the Cy3 label molecules experience a strong plasmonic coupling effect, leading to an increased SERS signal of the Raman labels upon laser excitation.

FIG. 1C illustrates the mechanism for the detection of particular nucleic acid sequences (target DNA) and that plasmonic coupling is interfered by the formation of LNA-target DNA duplexes. In this approach, the sequences of DNA probes (reporter-NPs) are designed to have the same sequence as the DNA targets. Therefore, the target DNA strands are then used as competitors of the reporter-NPs in a competitive binding process. As a result, the SERS signal is not enhanced as in FIG. 1B since the plasmonic coupling is interfered with by the target strands.

Figure 2B:
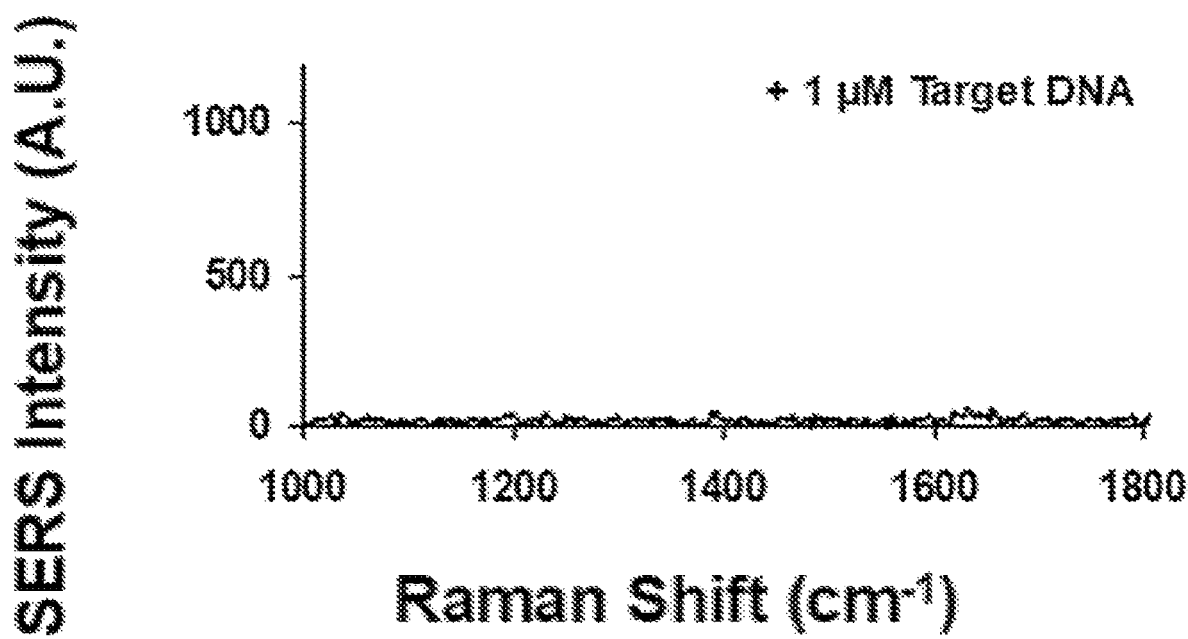
FIG. 2B illustrates a SERS spectra of Cy3 Raman peaks in the presence of 1 µM target DNA strands in a mixture of capture-NPs and reporter-Nps.

FIGS. 2A and 2B show the increased SERS intensity of the Cy3 Raman peaks in the presence of both capture-NPs and reporter-NPs (FIG. 2A) as compared to the SERS intensity in the presence of target DNA strands (FIG. 2B). The enhanced SERS signal indicates that the plasmonic coupling was induced by the hybridization reaction between the LNA and the labeled-DNA strands. To demonstrate the detection of DNA by using the concept of plasmonic coupling interference, capture-NPs and target DNA strands (1 μM) were mixed prior to the addition of a solution of reporter-NPs in order to ensure that the target DNA can effectively react with LNA strands. After adding reporter-NPs, the mixture was allowed to react for 20 min at room temperature and immediately followed by SERS measurements without washing steps. The spectrum in FIG. 2B shows the quenched SERS signal in the presence of target DNA strands in the mixture of capture-NPs and reporter-NPs, thus indicating that the plasmonic coupling effect was interfered with in the presence of target DNA strands. A dramatic color change from clear-grey to greenish yellow was observed over the course of 20 min indicating that AgNPs were aggregated in the absence of target DNA sequences. This color change result indicates the potential use of the NPCI approach as a simple and rapid screening tool using visual examination or rapid detection of color changes of the sample using a smartphone.

Figure 3:
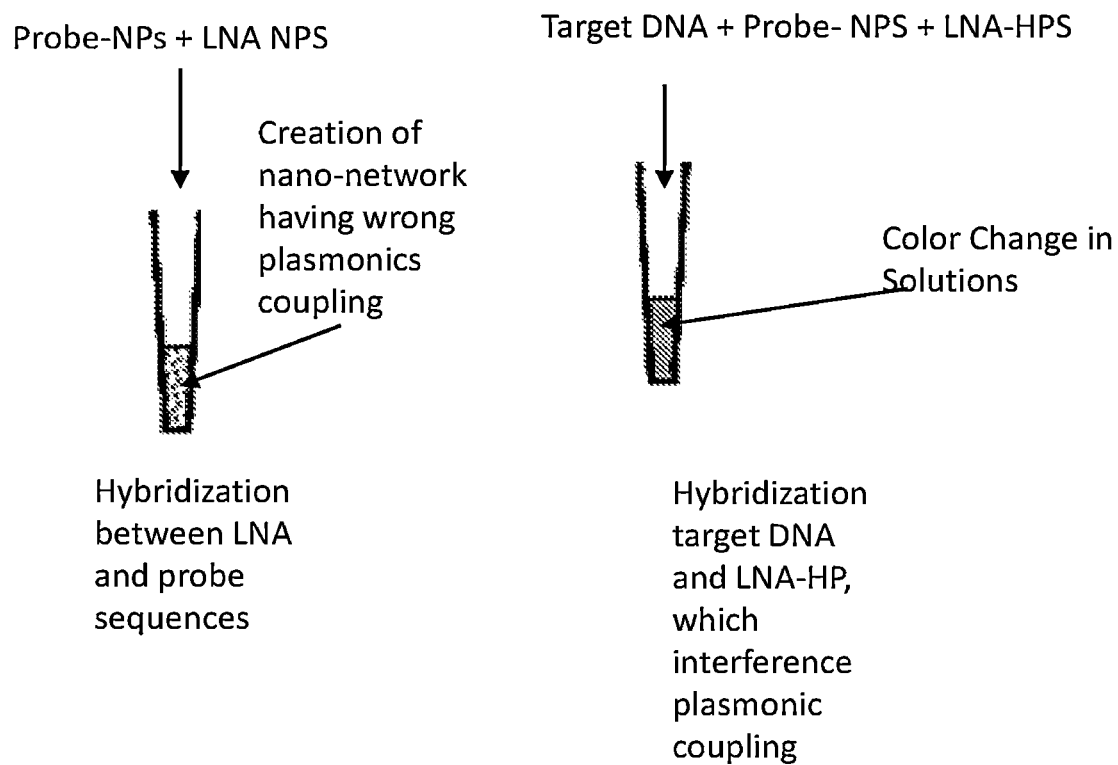
FIG. 3 illustrates a rapid diagnostic test based on NPCI using color change.

FIG. 3 illustrates the operating principle of rapid in vitro diagnostics using the NPCI modality. Color changes of solutions are used for rapid, simple, and inexpensive detection using smart phones. Rapid diagnostic testing, such as that enabled by the NPCI test described herein, is appropriate for environmental sensing applications (e.g., E coli in waste streams) and global health applications (infectious diseases) in underserved regions where access to sophisticated diagnostics facilities is not possible.

A mobile health device for detecting biomarkers is described herein. In an embodiment, the device comprises a sample housing including at least one slot, a cover, and a back plate that is removably attached to the mobile health device, an imaging sensor, and at least one processor. The at least one slot is operable to receive a sample container that contains a sample. The sample container received in the at least one slot is positioned to allow the image sensor to capture image data for the sample when the sample housing is attached to the mobile health device. The cover is positioned on a top side of the sample housing to block external light from entering the sample housing. The at least one processor is configured for receiving, from the image sensor, image data for the sample that is captured by the image sensor when the sample container containing the sample is received by the sample housing attached to mobile health device; and detecting at least one biomarker for the sample based on the received based on the image data.

Figure 4:
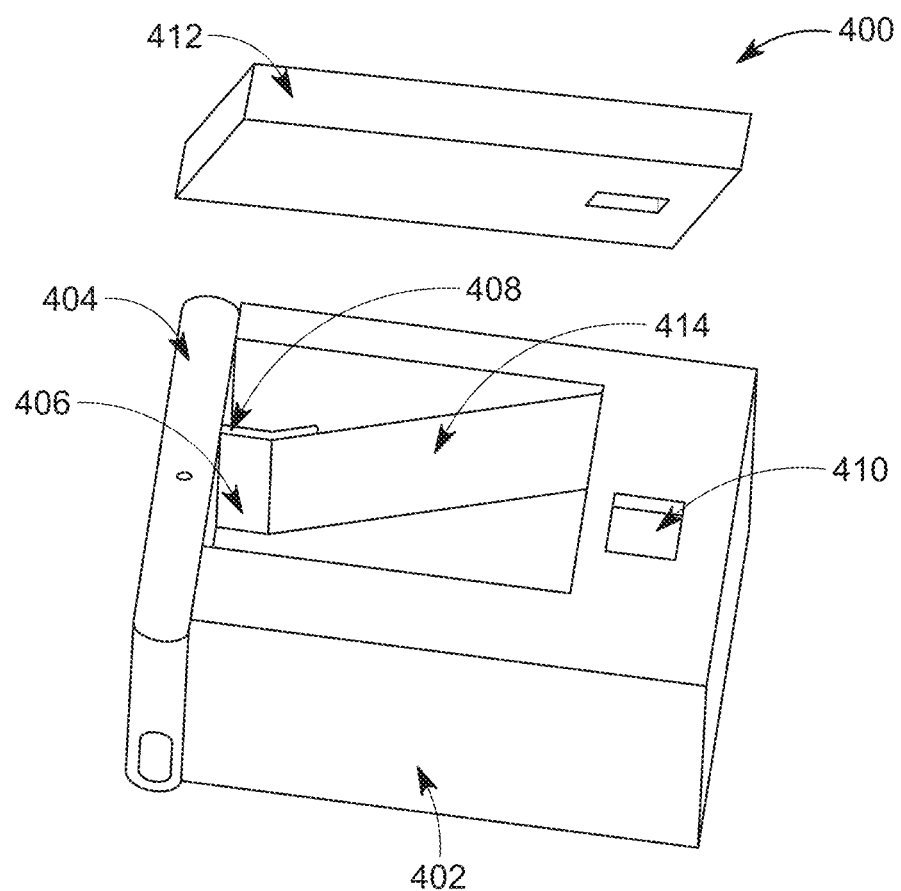
FIG. 4 illustrates an exploded perspective of a mobile health electronic device according to one embodiment of the present invention.
Figure 5:
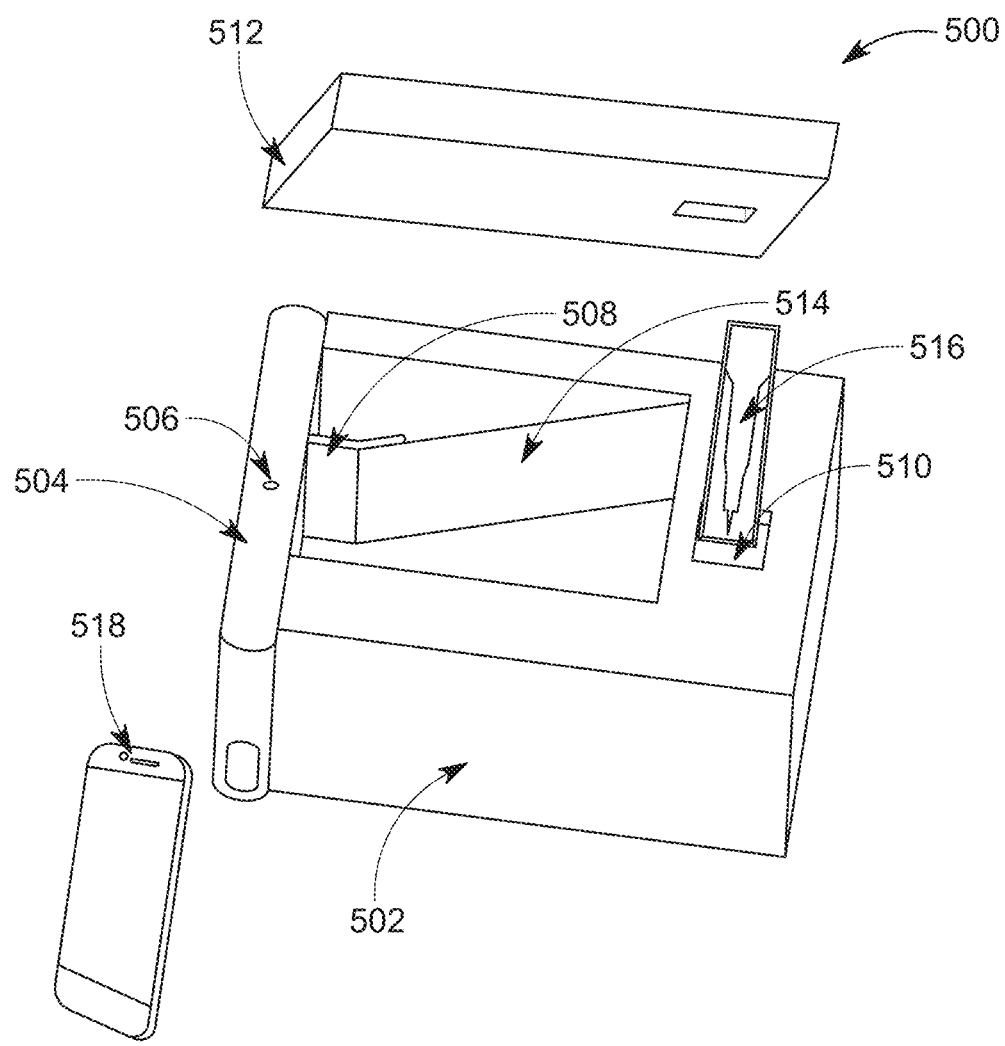
FIG. 5 illustrates an exploded perspective of a mobile health electronic device system receiving a microcuvette according to one embodiment of the present invention.

In an embodiment, the mobile health device includes a smartphone device and software platform. For example, and not limitation, the mobile health device may be referred to herein as "Krometriks." FIGS. 4 and 5 illustrate a Krometriks system consisting of a smartphone, a 3D printed accessory, and custom-built software deployed on the smartphone. The 3D printed accessory includes, but is not limited to, a half-case to hold the smartphone, a slot to hold the micro-cuvette, a partially opaque-partially-translucent (e.g., diffuser paper) curtain to diffuse light, and a background screen (e.g., white paper) (not shown). The smartphone's flash and camera act as the light source and the detector, respectively.

In one embodiment, as shown in FIG. 4, the Krometriks system 400 comprises a sample housing 402, an electronic device (e.g., smartphone—not shown), an electronic device holder 404, an opening for an image sensor 406 (image sensor may be e.g., camera), and space for illumination by at least one light source 408 (light source may be e.g., flash), and at least one processor (not shown).

The sample housing 402 is designed to removably attach to the electronic device. It may have dimensions of about 90 mm by 69 mm by 59 mm. The sample housing 402 includes at least one slot 410, a cover 412, and a curtain 414. The at least one slot 410 is operable to receive a sample container. For example, and not limitation, the at least one slot is operable to receive a microcuvette. When attached to the electronic device, the sample housing is positioned such that the at least one slot is at a distance of about 75 mm from an image sensor (e.g., camera) of the electronic device. While an exemplary distance of 75 mm is described herein. The skilled person will understand that other suitable distances may be used as appropriate, including, for example distances ranging from 70 mm to 80 mm. The cover 412 is designed to block external light from entering the sample housing. For example, and not limitation, the curtain includes a partially opaque-partially-translucent curtain 414 designed to diffuse light.

An important consideration for smartphone-based optical detection systems involves properly handling the effect of surrounding light. Devices using ambient light for image data acquisition, are subject to the inherent variability in the surrounding conditions between measurements. This issue has been addressed in the past through signal normalization using reference color areas and by enclosing the sample in a box/accessory to block outside light. In addition to performing normalization using a reference region, the device described herein also uses a custom-built 3D printed closed enclosure to hold samples.

The accessory holds samples in a fixed position with respect to the camera lens and inhibits relative movement between the smartphone and the sample between measurements. The accessory is intentionally designed to be simple and easy to use. Often, smartphone-based systems contain various optical and electrical parts as components of the accessory. These complex components are more challenging to maintain and repair, making them unpractical candidates for point-of-care applications. Many design decisions were made in view of intended use of the mobile health device for field applications in areas with limited resources. With small modifications to the accessory design, the mobile health device can be made compatible with different smartphone models and specifications.

As shown in FIG. 5, in one embodiment, the Krometriks device 500 includes a sample housing, an electronic device, an electronic device holder, and a cover. The Krometriks device 500 includes a sample housing 502, an electronic device (e.g., smartphone) 518, an electronic device holder 504, an opening for an image sensor 506 (image sensor may be e.g., camera), a space for illumination by at least one light source 508 (light source may be e.g., flash), and at least one processor. The sample housing 502 is designed to removably attach to the electronic device 518. The sample housing 502 includes at least one slot 510, a cover 512, and a curtain 514. The at least one slot 510 is operable to receive a sample container. For example, the at least one slot 510 is operable to receive a microcuvette 516. When attached to the electronic device, the sample housing is positioned such that the at least one slot is about 75 mm from an image sensor (e.g., camera) of the electronic device. The cover 512 is designed to block external light from entering the sample housing.

In an exemplary embodiment, the Krometriks device may include a smartphone (e.g., Samsung Galaxy S6, Samsung, South Korea), a smartphone accessory, and a dedicated mobile app. As described above, the sample housing comprises 3D printed parts, diffuser paper and white paper. The smartphone's in-built infrastructure provides a light source and a detector. The sample housing is easy to maintain, and the diffuser paper and white paper can be easily replaced if needed with little effort and low cost. Additionally, samples are measured in inexpensive disposable microcuvettes, making repeated use of the mobile device cost-effective.

To manage the process flow of the Krometriks device, a custom software application (app) was developed using an integrated development environment (Android Studio, Google) for the Android OS. The app is responsible for image data acquisition, preprocessing and processing of data, and result display in an automated fashion. In use, after the sample is placed in the slot in the enclosure and covered, the app is accessed. The app offers options to create a new calibration or to use an existing calibration to perform unknown sample analysis. Advantageously, the processor of the electronic device is designed to detect at least one biomarker based on image data corresponding to a sample positioned in the at least one slot. Alternatively, or additionally, the electronic device is in network communication with at least one computing device comprising at least one processor designed to detect at least one biomarker based on the image data.

When using the app, a set of reference samples with known concentrations of the analyte to be tested is used to create a calibration before performing any analysis. To create a new calibration, the corresponding option is selected on the mobile application. The calibration name can be input followed by data acquisition of the first calibration sample. The concentration value is input for the sample, after which the image data can be captured. A small red rectangle (20 by 40 pixels) on the camera preview indicates the region of interest, which is set to the middle of the sample. Only the pixels from the region of interest are considered while computing the color of the sample. A small blue square (35 by 35 pixels) over the white background on the camera preview indicates a reference region, which is also considered in the calculations to account for variations in illumination intensity between measurements. The mobile application captures color data from multiple images of the sample. The pixel data acquired by the smartphone is in the RGB color space and each pixel consists of three channels (red, green, blue). The pixels are in a 24-bit color system, each channel having 8 bits and an intensity value between 0-255 (28=256). Following the capture phase, the pixel values in the region of interest and over the multiple images are averaged to get a single color RGB value (color value) for the sample. The color value is then converted to the CIELAB color space. The data acquisition process as described above is performed for each calibration sample. Finally, the calibration data is sorted according to concentration values and stored in the phone's internal storage.

Figure 6A:
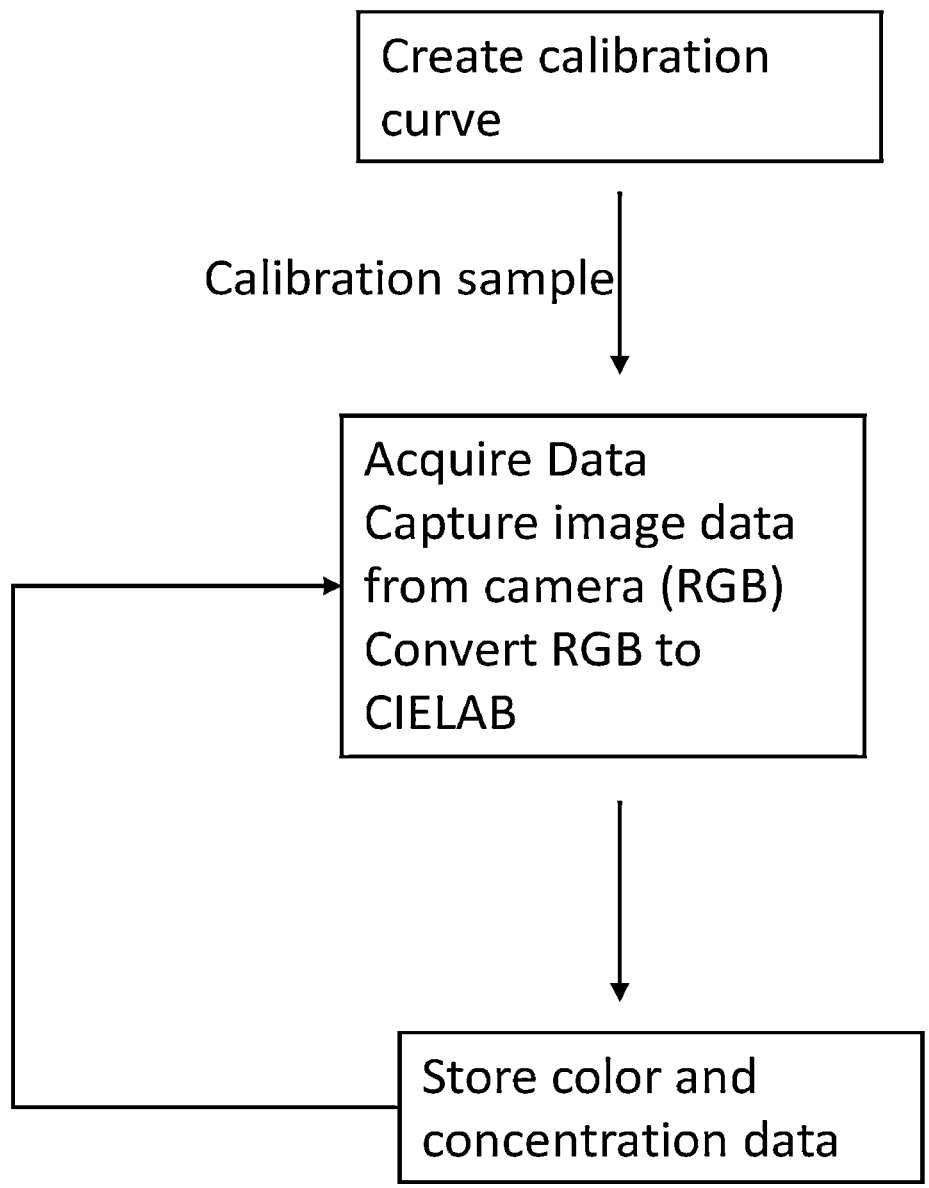
FIG. 6A is a schematic diagram of a calibration process according to one embodiment of the present invention.

FIG. 6A illustrates as schematic diagram of a calibration process according to an embodiment of the present invention. A calibration curve can be created after image data is acquired from an image sensor (e.g., camera). The image data can include RGB data. The RGB data is converted to CIELAB values. The color and concentration data are then stored.

Figure 6B:
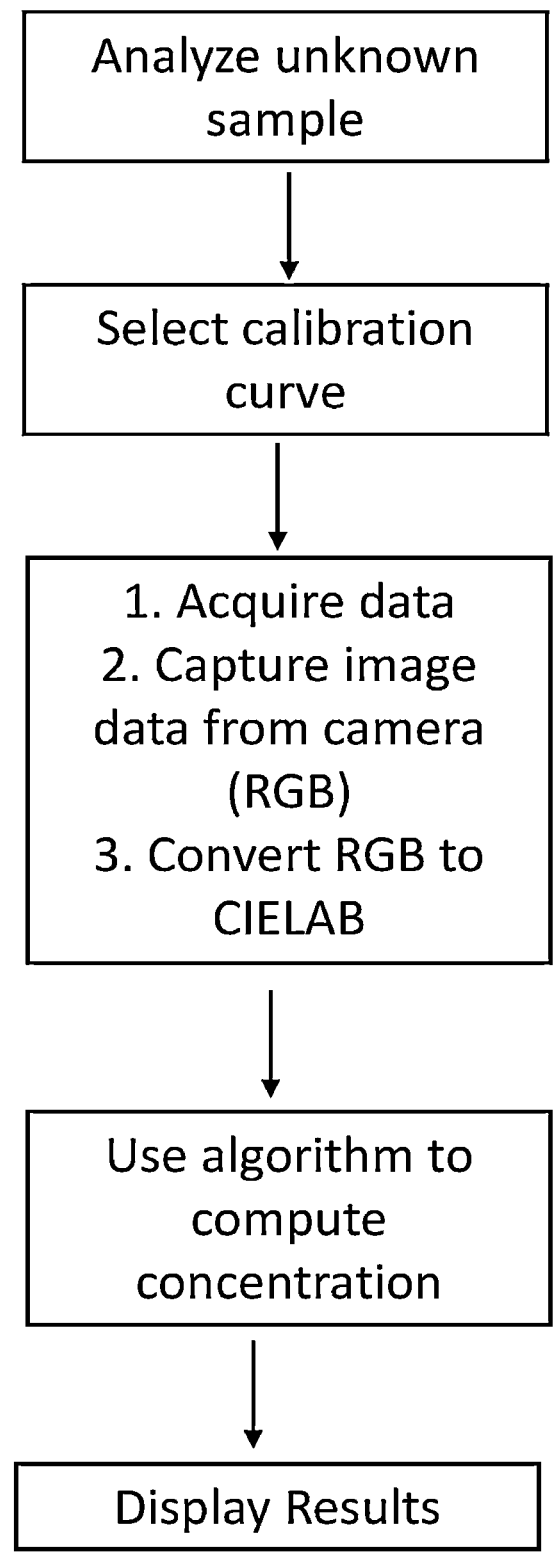
FIG. 6B is a schematic diagram of a colorimetric analysis of a sample according to one embodiment of the present invention.

FIG. 6B illustrates a schematic diagram of a sample analysis process according to an embodiment of the present invention. As described in greater detail below, samples can be prepared for measurement. Then, the app can be accessed to either create a calibration curve or analyze an unknown sample. As described above, establishing calibration data involves the use of reference samples with known concentration values. For sample analysis, a stored calibration curve is used along with a custom algorithm based on piecewise linear interpolation to calculate the value of the unknown concentration. Data acquisition and pre-processing follow the same procedure for both calibration and test samples. For each sample, the color of the sample is measured using the smartphone's camera. A single color for the sample is determined by averaging the pixels in the region of interest (ROI), normalizing with pixels from the reference region, followed by its conversion from the RGB to the CIELAB color space (see FIG. 6C for a schematic).

The CIELAB space is used because it is device-independent and perceptually uniform. Each color can be represented by a point in three-dimensional Euclidean space with L*, a* and b* as the three coordinates. The Euclidean representation of CIELAB colors renders a fixed definition for measuring color difference: taking the Euclidean distance between the points. This is advantageous as the color difference definition is independent of analyte type or assay conditions and can be used unprejudiced with different assays and analytes. After the conversion of image data to the CIELAB color space, the information is either stored (for calibration samples) or analyzed (for test samples). Following analysis, quantification results are displayed. Sample analysis (data acquisition to result display) only takes a few clicks and a few minutes of the user's time, providing a rapid output with minimal user input.

The CIELAB color space, also referred to as L*a*b*, is a color space defined by the International Commission on Illumination in 1976. The CIELAB color space has three channels represented by L*, a* and b*. L* represents the lightness, with values ranging from 0 denoting black to 100 denoting white. The a* channel represents the magenta-green spectrum position with negative values indicating green and positive values indicating magenta. The b* channel represents the position on the blue-yellow spectrum, positive values denoting yellow and negative values denoting blue. Conversion from RGB to CIELAB space involves the following four steps:

1. The RGB value (R, G, B) is normalized ($R_n$, $G_n$, $B_n$) to a value in the range [0, 1].

2. The normalized non-linear RGB values are linearized ($R_l$, $G_l$, $B_l$) with the following equation:

$$C_l = \left\{ \begin{array}{ll} \left(\dfrac{C_n + 0.055}{1.055}\right)^{2.4} & :C_n > 0.04045 \\ \dfrac{C_n}{12.92} & :C_n \leq 0.04045 \end{array} \right\}$$

where $C \in \{R, G, B\}$

3. The linearized RGB values are converted to tristimulus values (X, Y, Z) under standard illuminant D65 through these three associations:

$$X = 0.4124 R_l + 0.3576 G_l + 0.1805 B_l$$

$$Y = 0.2126 R_l + 0.7152 G_l + 0.0722 B_l$$

$$Z = 0.0193 R_l + 0.1192 G_l + 0.9505 B_l$$

4. The tristimulus values (X, Y, Z) are multiplied by a factor of 100 and then used to compute the CIELAB values (L*, a*, b) using the following equations:

$$L^* = 116 f\left(\dfrac{X}{X_n}\right) - 16$$

$$a^* = 500 \left( f\left(\dfrac{X}{X_n}\right) - f\left(\dfrac{Y}{Y_n}\right) \right)$$

$$b^* = 200 \left( f\left(\dfrac{Y}{Y_n}\right) - f\left(\dfrac{Z}{Z_n}\right) \right),$$

where $$f(x) = \left\{ \begin{array}{ll} \sqrt[3]{x} & :x > (6/29)^3 \\ (841/108)x + 4/29 & :x \leq (6/29)^3 \end{array} \right\}$$

and $X_n = 95.047$, $Y_n = 100$ and $Z_n = 108.883$ are the tristimulus values of the white point of standard illuminant D65 using the 2° standard observer and normalized for relative luminance.

When using the mobile application, prior to choosing the option for sample analysis, the corresponding calibration is selected from the list of stored calibrations on the application. The image acquisition and color determination for the test sample follows the process described above for the calibration samples. The following algorithm is then used to quantify the concentration of the test sample:

1. The test point is compared to each data point in the stored calibration curve. Comparison takes place by calculating the color difference between the two points. Color difference is calculated by taking the Euclidean distance between the color points using the following equation:

$$d_{12} = \sqrt{(L_2^* - L_1^*)^2 + (a_2^* - a_1^*)^2 + (b_2^* - b_1^*)^2}$$

where $L_1^*$, $a_1^*$, $b_1^*$ and $L_2^*$, $a_2^*$, $b_2^*$ are the CIELAB components of the color points respectively. The distance between each calibration point and the test point is calculated and the calibration point corresponding to the smallest distance is noted. This point is $p_n$, where n is the index of the point in the list of sorted calibration points.

2. The distance between the test point and calibration points $p_{n-1}$ and $p_{n+1}$ is calculated and the smaller of the two is noted ($p_{n-1}$ and $p_{n+1}$ are the two adjacent points to $p_n$ on the sorted calibration. If $p_n$ is the first or the last point on the calibration, then the sole adjacent point is noted). This point is represented by y, $p_n$ by x and the test point by z, henceforth.

3. The concentrations corresponding to x, y and z are denoted by $C_x$, $C_y$ and $C_z$, respectively. A linear gradient is assumed between the successive calibration points. Interpolating between x and y, the point on the line joining x and y that is closest to point z is located and its distance to point x (denoted by D) is calculated (FIG. 6C for visual representation) using the equation:

$$D = \frac{d_{xy}^2 + d_{xz}^2 - d_{yz}^2}{2d_{xy}}$$

4. The test sample concentration $C_z$ is calculated using the equation:

$$C_z = C_x + \frac{(C_y - C_x)D}{d_{xy}}$$

Samples to be analyzed by the mobile device can be prepared using known methods. For example, oligonucleotide conjugated silver nanoparticles (AgNP-oligoA and AgNP-oligoB) can be prepared using known methods. For example, samples can be prepared by mixing 10 µL of AgNP-oligoA and AgNP-oligoB each with 10 µL of a target probe in 20 µL water. To this mixture, 50 µL of a buffer solution with a final concentration of 0.15 M sodium chloride, 2.5 mM magnesium chloride, 10 mM Tris-HCl (pH 8.0) and 0.01% Tween 20 can be added and incubated for 60 min. Following incubation, a custom stopper sequence designed to stop the reaction between AgNP-oligoA and the target probe for a few hours can be added and the sample measured.

Figure 6C:
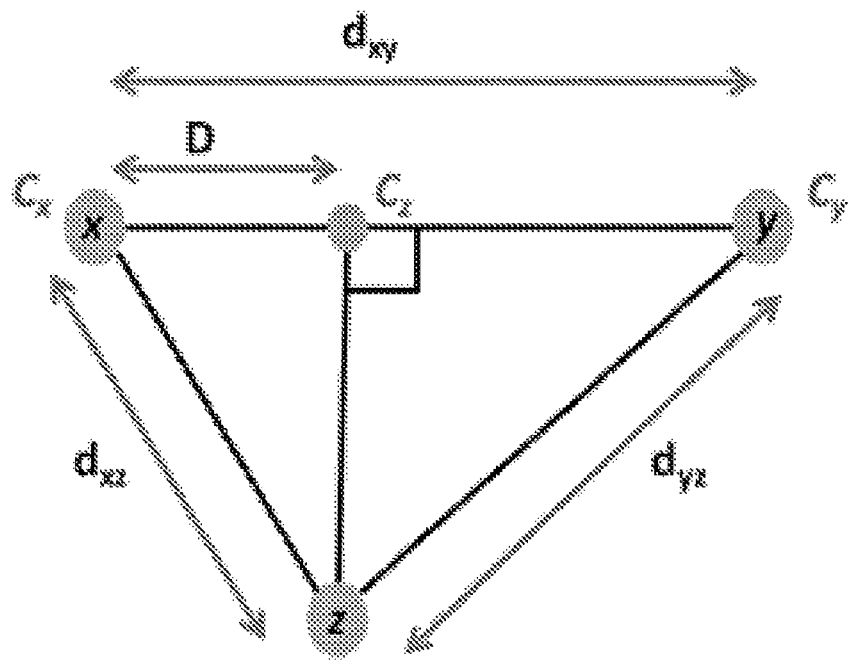
FIG. 6C is a schematic diagram illustrating the relationship between sample points and calibration points according to one embodiment of the present invention.

FIG. 6C illustrates the relationship between x, y, and z, wherein z is the test sample point, and x and y are the calibration points closest to z. Interpolation of the concentration Cz is shown on the line between Cx and Cy. The software application is designed to receive user input via a user interface of an electronic device (e.g., smartphone). For example, and not limitation, the device described herein is designed to receive a new data point during a calibration creation and display test sample analysis, new calibration creations results, test sample analysis and results of the test sample analysis.

Figure 6D:
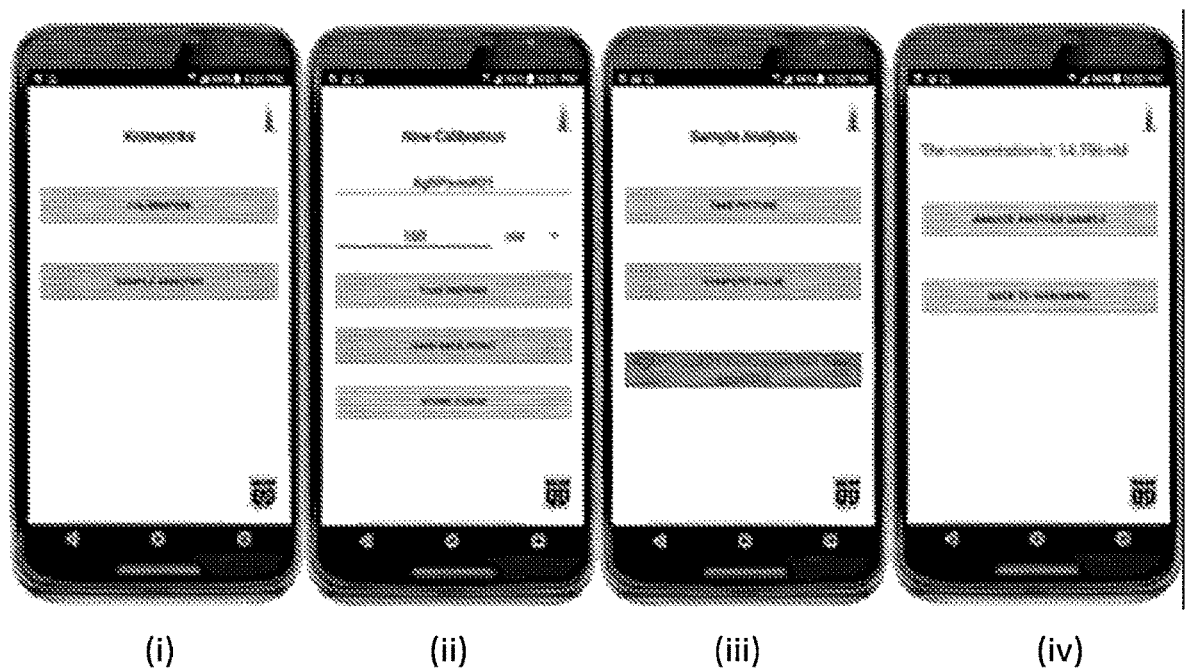
FIG. 6D shows a set of exemplary screenshots from a mobile application according to one embodiment of the present invention.

FIG. 6D is a set of exemplary screenshots from the Krometriks app showing: (i) the main menu, (ii) the menu for adding a new data point during new calibration creation, (iii) the page for test sample analysis and (iv) display of the result.

2.5. Statistical Analysis

Comparison of the estimation accuracy of Krometriks and the spectrophotometer was performed by calculating and comparing the estimation error (i.e., a large error corresponds to a low accuracy) using the following equations:

$$\text{Absolute Percentage Error} = \left|\frac{\text{Actual} - \text{Estimated}}{\text{Actual}}\right| \times 100$$

$$\text{Mean Absolute Percentage Error } (MAPE) = \frac{1}{n}\sum_{i=1}^{n} APE_i$$

where Actual is the actual value of the sample, Estimated is the estimated value of the sample, and n is the total number of samples To determine the difference in estimation accuracy between two methods, a statistic test based on the two proportion Z-test was performed using the following equation:

$$Z = \frac{MAPE_2 - MAPE_1}{\sqrt{2 * MAPE_{avg}(100 - MAPE_{avg})/n}}$$

where $$MAPE_{avg} = \frac{MAPE_1 + MAPE_2}{2}$$

and $MAPE_1$ and $MAPE_2$ are the mean absolute percentage error of method 1 and method 2, respectively, and n is the number of samples.

Based on a standard normal distribution with a 5% level of significance, if Z<−1.645, then we can say with 95% confidence that method 2's estimation accuracy is more than that of method 1. If Z>1.625, then we can say with 95% confidence that method 1's estimation accuracy is more than that of method 2. Otherwise, if −1.625<Z<1.625, then there is no significant difference (for a 5% level of significance) in the estimation accuracy between method 1 and method 2.

Smartphones have been used to detect vitamin-D, cocaine, cancer antigen, and lidocaine hydrochloride in vitreous humor with gold and silver nanoparticle-based colorimetric assays. The utility of Krometriks was tested by performing colorimetric analysis on a nanoparticle-based assay for nucleic acid detection. The testing demonstrated the usefulness of the Krometriks device to analyze microRNAs (miRNAs), which have been shown to serve as useful biomarkers of a wide variety of illnesses, ranging from cancers and cardiovascular illnesses to infectious diseases. Furthermore, miRNA biomarkers have also exhibited significance in non-medical application areas such as plant biology and renewable biofuel research. For instance, recent studies in plants indicated that miRNAs can target squamosa promoter binding protein-like (SPL) genes and define a separate endogenous flowering pathway, which is important in biofuel research as the timing to flower is one of the key determinants to plant biomass accumulation and agricultural yields. It is contemplated that Krometriks could provide a practical tool to perform plant analysis under field conditions.

Briefly, in the nanoparticle-based assay for nucleic acid detection, silver nanoparticles (AgNPs) were conjugated with two complementary oligonucleotide probes, probe-A and probe-B respectively. When mixed, probe-A and probe-B hybridized with each other leading to AgNP aggregation. Addition of a complementary target probe resulted in a competition between the target probe and probe-B to bind to probe-A. A higher concentration of the target probe in the mixture caused lesser probe-A and probe-B binding resulting in lesser AgNP aggregation. The extent of AgNP aggregation determines the color of the solution and the profile of the absorption spectrum. Target probe concentration was thus estimated by quantifying the color of the aggregated AgNP solution and comparing it to a calibration curve.

To test the accuracy of the device, a known cancer biomarker miR-21 was chosen as the target for the assay. Samples containing different target probe concentrations were first evaluated with a spectrophotometer, which is most widely used modality for colorimetric measurements. It was observed from the absorption spectra in the UV-Vis region (300-800 nm) (FIG. 7) measured using a microplate reader (FLUOstar Omega, BMG LABTECH, Germany) that an increase in the miR-21 target probe concentration caused an increase in the absorbance maximum value indicating lesser AgNP aggregation.

The testing results demonstrated the usefulness of the Krometriks device to analyze microRNAs (miRNAs). miRNAs hold great potential to serve as an important class of biomarkers not only for early diagnosis of cancer, but also for investigation of cancer initiation and progression. It is noteworthy that miRNA biomarkers also exhibit significance in non-medical application areas as well. For instance, recent studies in plants indicated that miRNAs can target squamosa promoter binding protein-like (SPL) genes and define a separate endogenous flowering pathway, which is important in biofuel research as the timing to flower is one of the key determinants to plant biomass accumulation and agricultural yields. The Krometriks device could provide a practical tool to perform simple plant analysis under field conditions.

Figure 7:
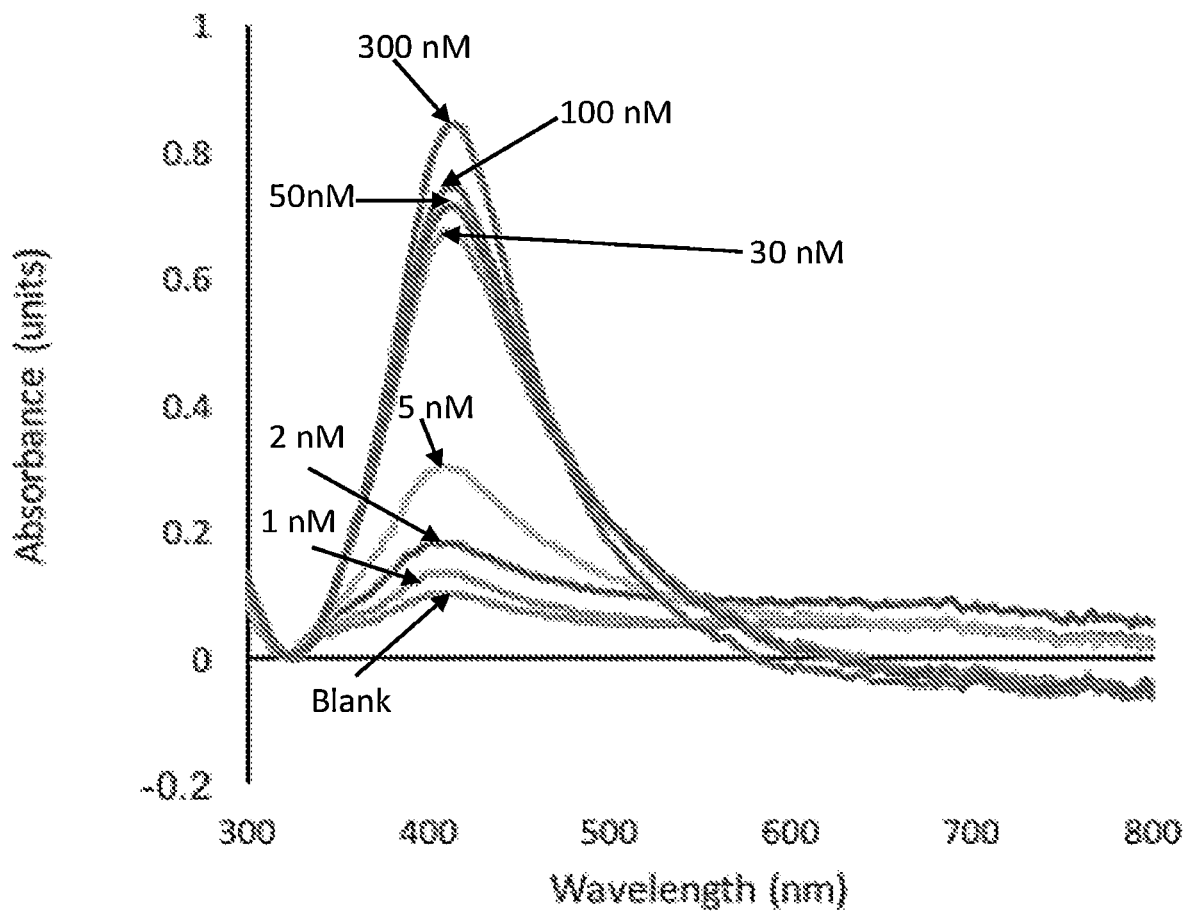
FIG. 7 illustrates an absorption spectra of samples with different microRNA-21 target probe concentrations.
Figure 8:
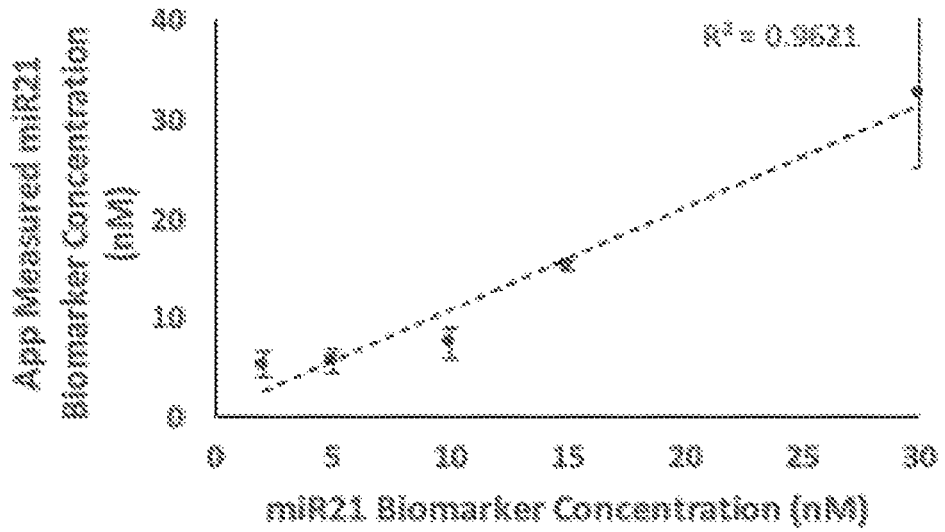
FIG. 8 illustrates estimated concentration values of a mobile health electronic device system of one embodiment of the present invention against the actual concentration value of samples with different microRNA-21 target probe concentrations.

Test samples with different concentrations of the miR-21 target probe (2 nM-30 nM) were tested multiple times with the Krometriks device. FIG. 7 shows an absorption spectra of samples with different miR-21 target probe concentrations. FIG. 8 illustrates an estimated concentration values versus the actual concentration values of samples with different miR-21 target probe concentrations using the Krometriks device. The comparison plot of the FIG. 8 shows that the colorimetric quantification capability of the Krometriks device is reasonably accurate and demonstrates the potential for diagnostic testing.

Figure 9A:
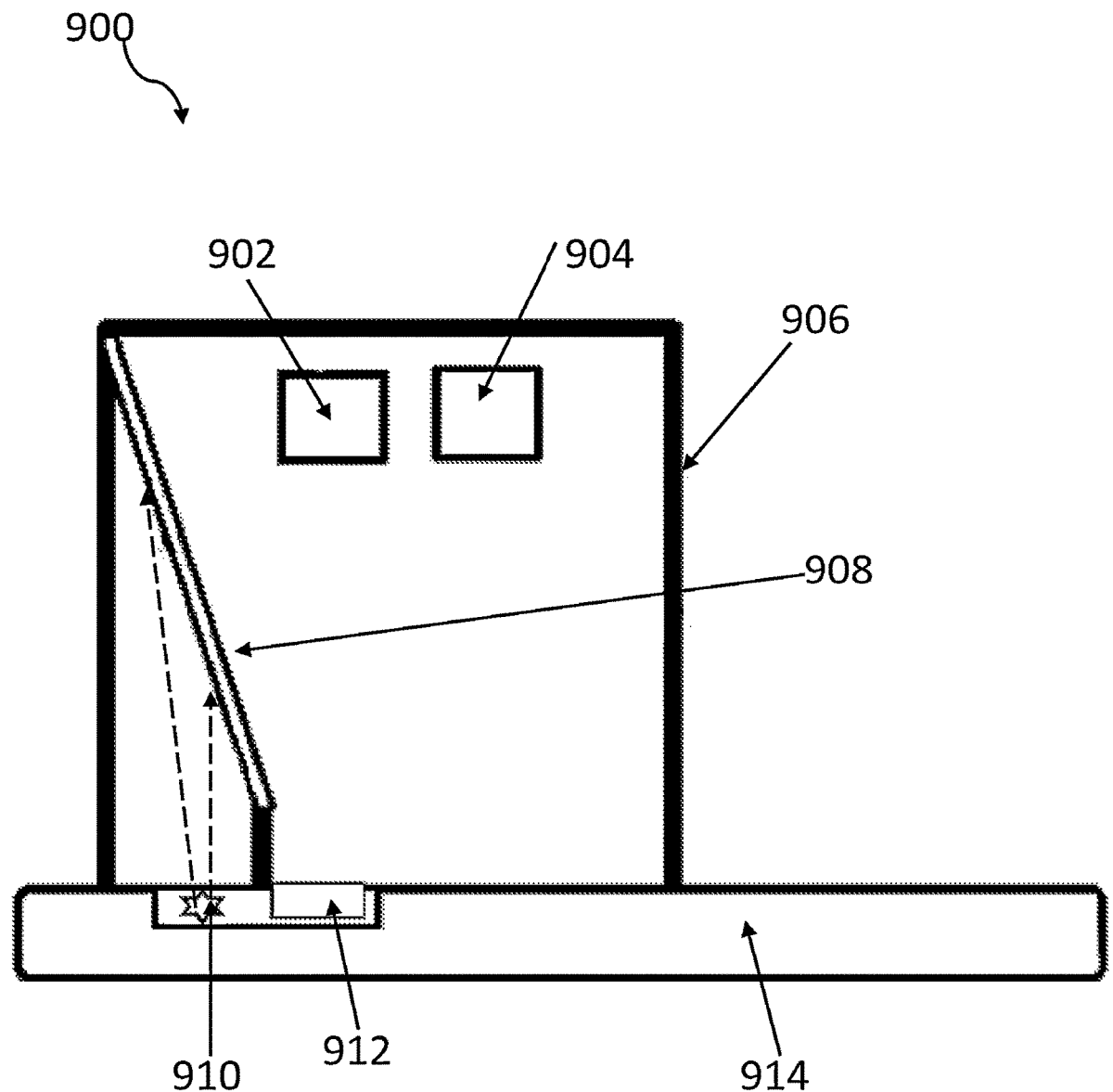
FIG. 9A is a top view schematic diagram representing a smart phone platform design for colorimetric assays of liquid samples.
Figure 9B:
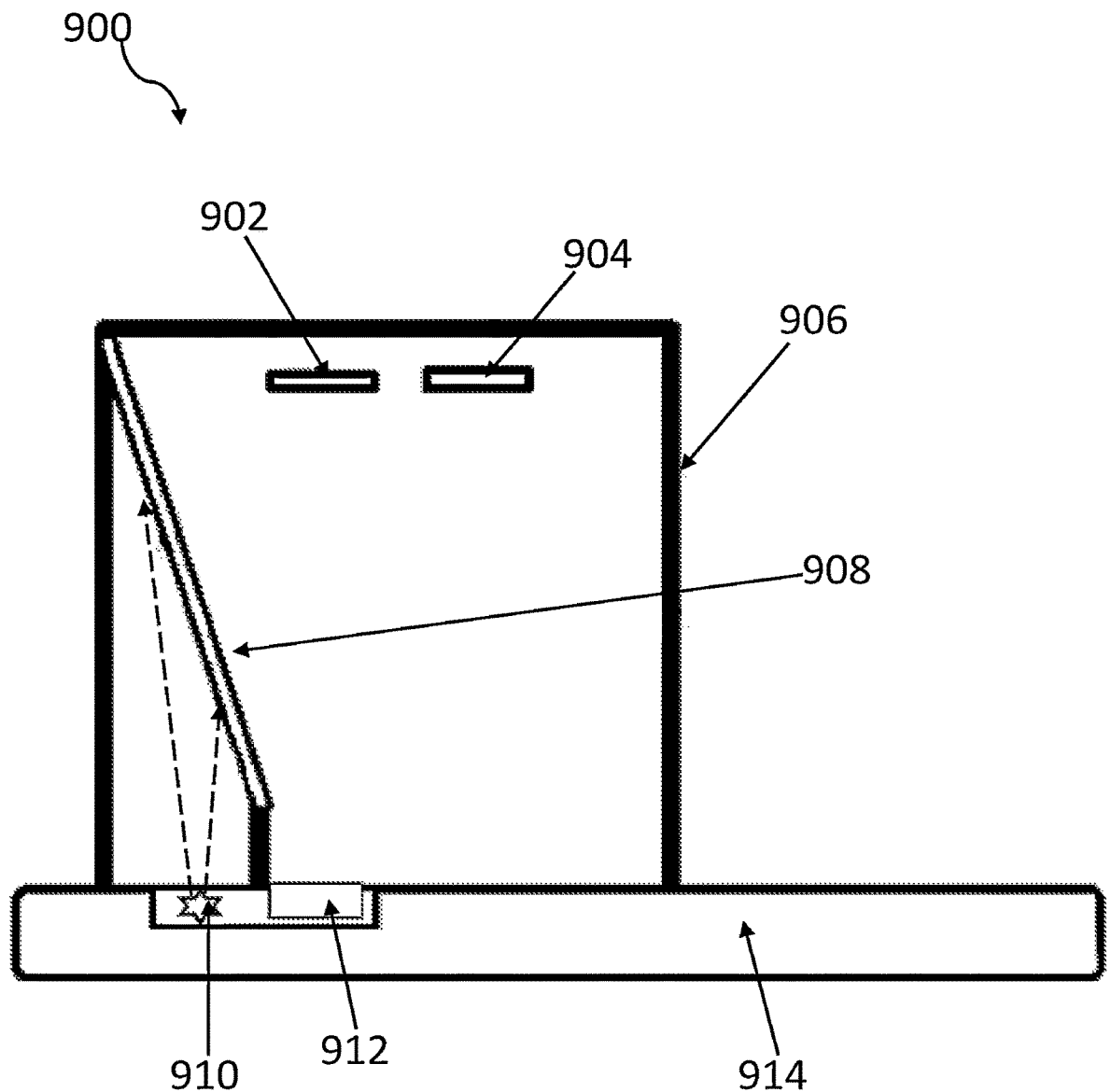
FIG. 9B a top view schematic diagram representing a smartphone platform design for colorimetric assays of solid samples.

The mobile diagnostic device described above had one sample holder. An alternative design can have two sample holders, one for the sample and one for a reference (FIG. 9A). FIG. 9B shows a design of a mobile health system capable of use for analyzing solid surface samples (e.g., paper strip, microplate, solid substrate, or chip, etc.). As shown in FIG. 9A, the mobile health system for colorimetric assays of liquid samples can include a reference solution 902, a sample 904, a sampling enclosure 906, a light diffuser plate 908, a light source 910 (e.g., flashlight, light emitting diode (LED)), a camera 912, and a mobile phone base 914. As shown in FIG. 9B, the mobile health system for colorimetric assays of solid samples can include a reference solid surface, a sample, a sampling enclosure, a light diffuser plate, a light source (e.g., flashlight, light emitting diode (LED)), a camera and a mobile phone base.

Figure 10A:
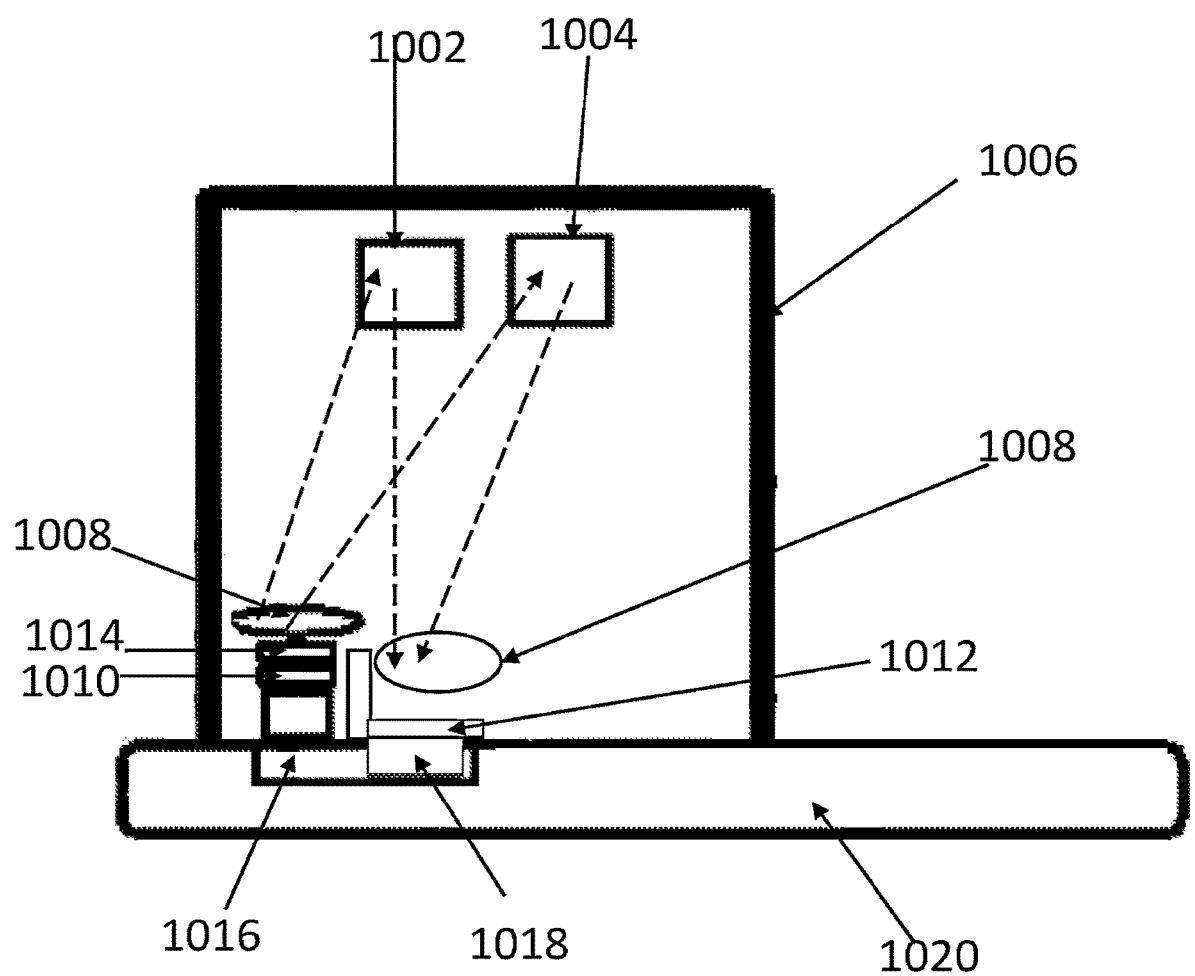
FIG. 10A a top view schematic diagram representing a smartphone platform using Raman scattering detection for analyzing liquid samples.
Figure 10B:
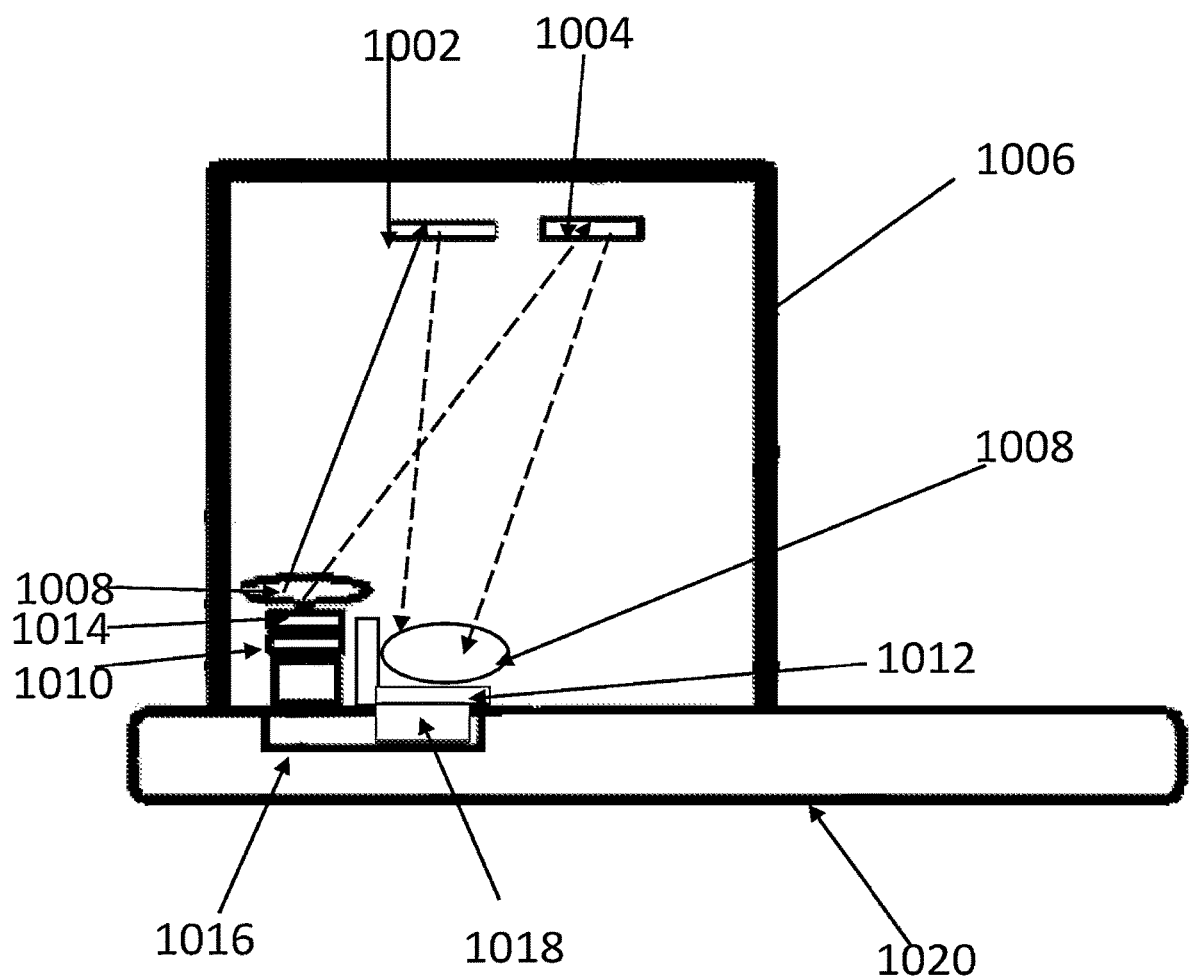
FIG. 10B a top view schematic diagram representing a smartphone platform using Raman scattering detection for analyzing solid samples.

FIGS. 10A and 10B show the design for a mobile health system using Raman scattering detection for analyzing liquid samples (FIG. 10A) and solid surface samples (e.g., paper strip, microplate, solid substrate, or chip, etc.) (FIG. 10B). In one embodiment, the mobile health system for Raman scattering includes a reference solution 1002, a sample 1004, a sample enclosure 1006, optic components 1008, bandpass excitation filter 1010, bandpass emission filter 1012, a notch filter 1014, a light source 1016 (e.g., miniaturized laser, Vertical Cavity Surface Emitting Laser (VECSL), laser diode, etc.), a camera 1018, and a mobile phone base 1020. Alternatively, the mobile health system for Raman scattering does not include a reference solution. For Raman assay, a monochromatic light source (e.g., miniaturized laser, VECSL, laser diode, etc.) can be used for excitation. The excitation bandpass filter is used to select the wavelength of the excitation light (not required for a laser that emits narrow emission lines). A notch filter (required) is used to spectrally "isolate" the laser emission line. The emission bandpass filter is used select the wavelength of the sample emission (i.e., Raman scattering)

Figure 11:
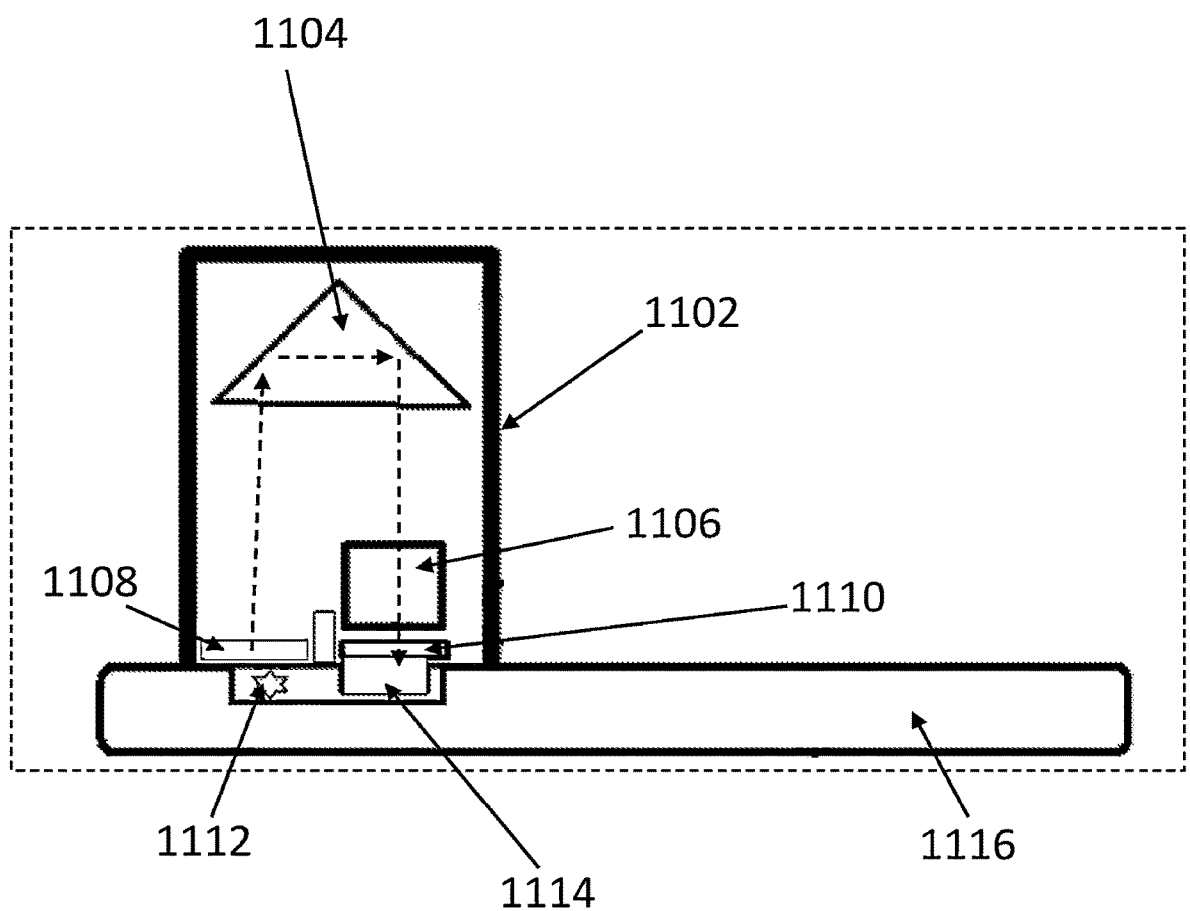
FIG. 11 a top view schematic diagram representing a smartphone platform design for Raman assays of liquid samples.

FIG. 11 shows the design for a mobile health system using absorption detection for analyzing liquid samples. The mobile health system includes a sampling enclosure 1102, prism and/or mirror system 1104, a sample 1106, an excitation filter 1108, an emission filter 1110, a light source 1112 (e.g., flashlight, LED, VECSL, laser diode, etc.), camera 1114, and a mobile phone base 1116. The prism and/or mirror system is designed to reflect and transmit light through the sample for absorption measurements.

Figure 12:
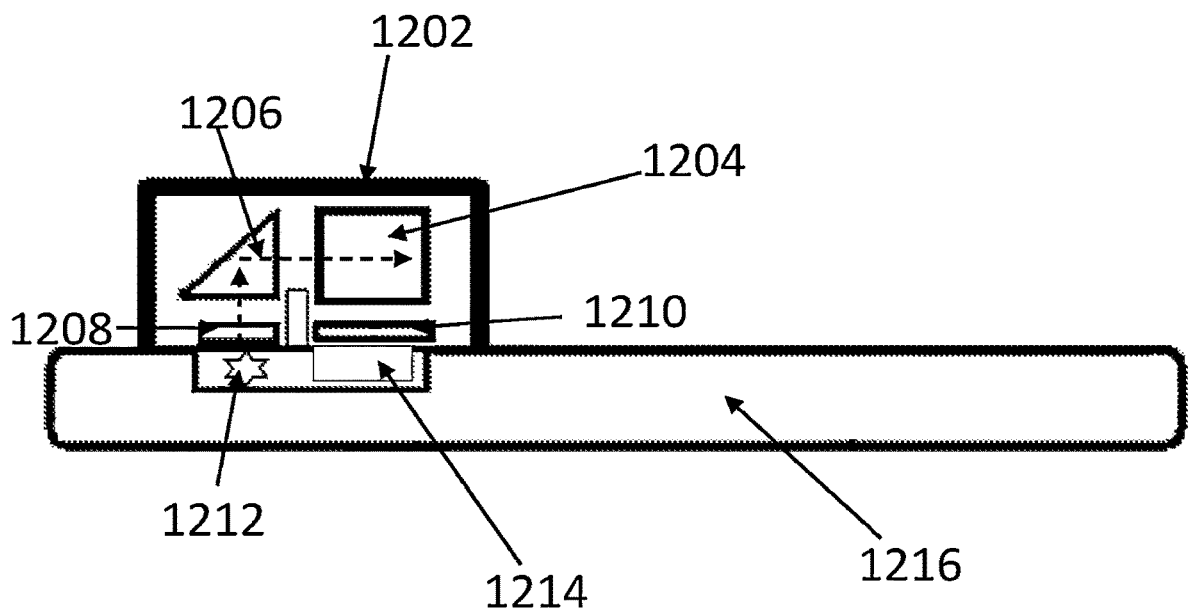
FIG. 12 a top view schematic diagram representing a smart phone platform design for emission assays of liquid samples.

FIG. 12 shows an exemplary design for a mobile health system using emission (luminescence, fluorescence, phosphorescence) detection for analyzing liquid samples. The mobile health emission detection system for analyzing liquid samples includes a sample enclosure 1202, a sample 1204, a prism or mirror system 1206, an excitation filter 1208, a bandpass emission filter 1210, a light source 1212, (e.g., flashlight, LED, VECSL, laser diode, etc.), a camera 1214, and a mobile phone base 1216. The prism or mirror system is designed to reflect and perpendicularly excite the sample for emission measurements. The excitation bandpass filter is used to select the wavelength of the excitation light (not required for a laser that emits narrow emission lines). A notch filter (optional) is used to spectrally isolate the laser emission line. The emission bandpass filter is used to select the wavelength of the sample emission.

Figure 13:
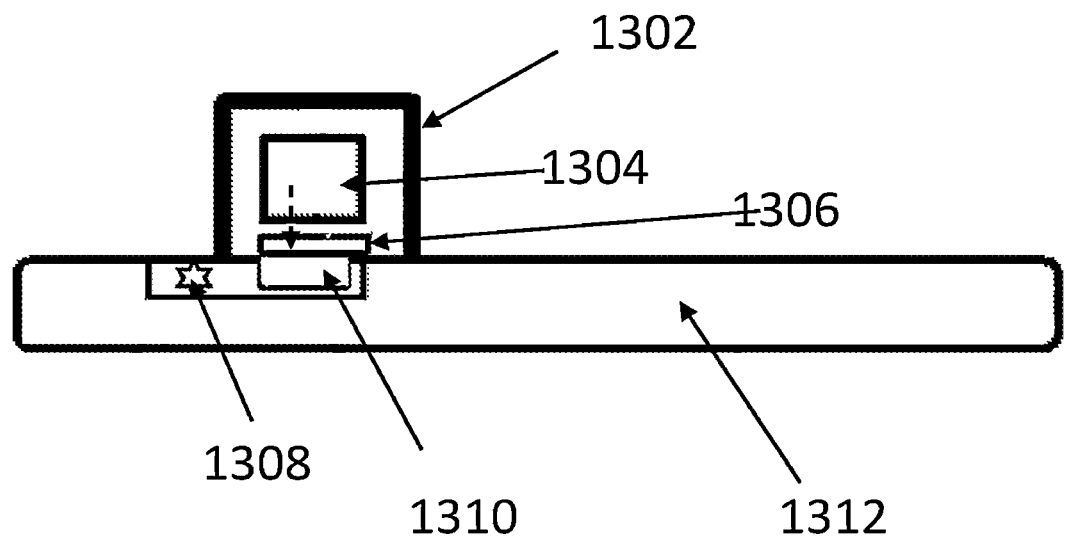
FIG. 13 a top view schematic diagram representing a smart phone platform design for bioluminescence assays of liquid samples.

FIG. 13 shows an exemplary design for a mobile health system using emission (luminescence, fluorescence, phosphorescence) detection for analyzing liquid samples. The mobile health emission detection system for liquid samples includes a sample enclosure 1302, a sample 1304, a bandpass emission filter 1306, a light source 1308, a camera 1310, and a mobile phone base 1312. In one embodiment, the sample includes a bioluminescent sample, and the mobile health system does not include a light source. The emission bandpass filter is used to select the wavelength of the sample emission.

Figure 14:
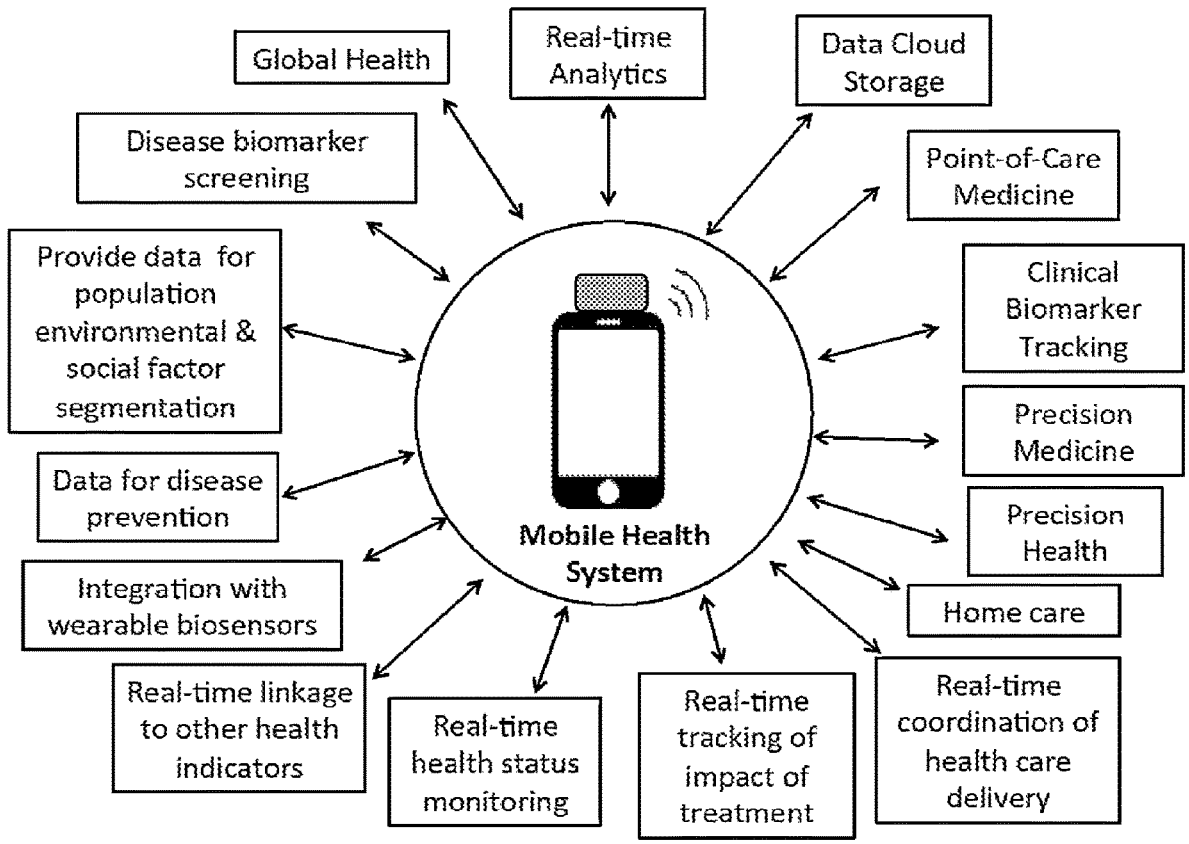
FIG. 14 is a schematic diagram of a software platform according to one embodiment of the present invention.

FIG. 14 illustrates a mobile health platform according to one embodiment of the present invention. The mobile health platform is designed for a plurality of application including, but not limited to, global health, point-of-care medicine, clinical biomarker tracking, precision medicine, precision health, home care delivery, real-time tracking of impact of treatment, real-time health status monitoring, real-time linkage to other health indicators, integration with wearable biosensors, data for disease prevention, provide data or population environmental and social factor segmentation, and disease biomarker screening. The proposed mobile health system can also be applied to other non-medical applications. The results also indicate that this new label-free assay has potential for a wide variety of applications based on DNA/RNA/protein detection including, but not limited to, biomedical applications, point-of-care diagnostics, environmental monitoring, industrial process sensing, quality control applications, biotechnology industrial control, quality control, global health, cancer research. heart disease diagnostics, and homeland defense.

Example

A smartphone-based biosensing device for miRNA detection and quantification is described. The device, referred to as Krometriks, includes a smartphone with a 3D printed accessory and custom-built software integrated into and deployed on the smartphone. A silver nanoparticle (AgNP)- based assay, referred to as plasmonic coupling interference (PCI), developed for multiplex nucleic acid biomarker detection was adapted for colorimetric sensing. When metallic nanoparticles aggregate, due to an effect known as plasmonic coupling, their absorbance and scattering pattern changes, leading to a change in color and absorption spectra. This optical behavior exhibited by nanoparticles has been utilized in the colorimetric detection of metal ions and biomolecules.

In the PCI assay, the extent of nanoparticle aggregation in solution is determined by the amount of miRNA targets present in the sample being monitored. miRNA quantification is achieved by measuring the associated color change of the solution. A Krometriks device can be used with synthetic microRNA-21 (miR-21) as the target molecule. miR-21 is a known biomarker that has been reported to be dysregulated in breast, colon, lung and various different types of cancer and non-cancer diseases, including cardiovascular, infectious, and neurological diseases. Krometriks can measure nanomolar concentrations of the miRNA target requiring very small amounts (100 μL) of the sample in an automated fashion. The detection accuracy of Krometriks is shown to be comparable to that of a benchtop spectrophotometer. Krometriks is portable, simple to use, has a simplistic design and performs automated analysis. Such a system has the potential to be a useful colorimetric tool for clinical diagnostics in the context of point-of-care and global health applications.

Figure 15:
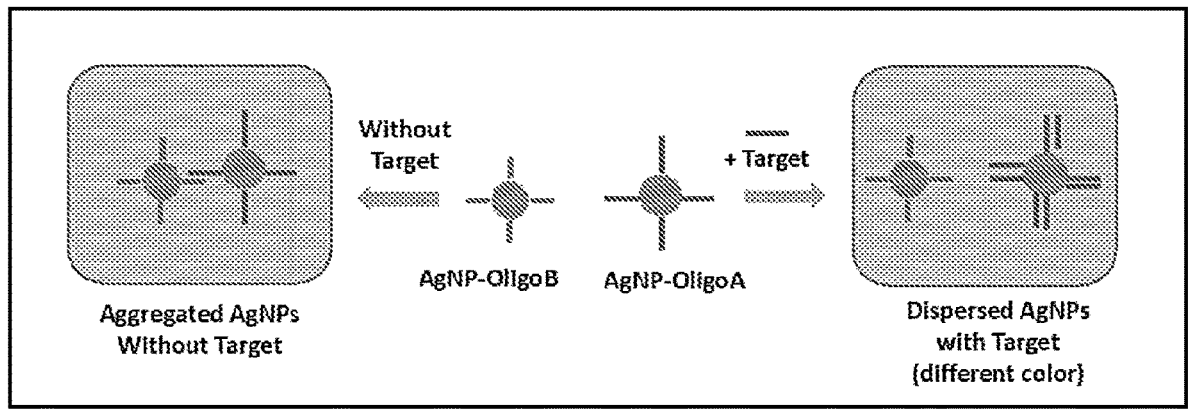
FIG. 15 is a schematic diagram showing the operating principle of a colorimetric sensing method using nanoparticle-base assay according to one embodiment of the present invention.

The operating principle of the plasmonic nanoparticle-based detection method described in previous works is schematically shown in FIG. 15. This approach involves two nanoprobe constructs, probe-A and probe-B, prepared for one specific miRNA sequence. Probe-A is designed to be complementary to a specific miRNA sequence as a capture probe. To induce aggregation, probe-B is designed to have sequences complementary to the probe-A, leading to nanoparticle aggregation (FIG. 15, left). This approach then utilizes the target sequences as competitors of the probe-B in a competitive binding process. As a result, the aggregate formation of nanoparticles is disrupted by the target molecules (FIG. 15, right), resulting in a shift of the plasmon resonance band, leading to sample color changes depending on the aggregate size.

Briefly, silver nanoparticles were prepared and conjugated to two oligonucleotide sequences (oligoA and oligoB) specific to miR-21. Silver nanoparticles were prepared by swiftly adding 1 mL of a solution containing 15 mM hydroxylamine hydrochloride and 30 mM sodium hydroxide to 9 mL of 1.1 mM silver nitrate solution under vigorous stirring conditions for 1 hr. The colloidal solution was kept at 4° C. and used within a few weeks.

Final samples were prepared by mixing AgNP-oligoA and AgNP-oligoB nanoprobes in a 1:1 volume ratio with the synthetic miR-21 target (5'-TAGCTTATCAGACT-GATGTTGA-3'). Silver nanoparticles were incubated with 0.4 μM thiolated DNA oligonucleotides (oligoA having the sequence 5'-SH-TCAACATCAGTCTGATAAGCTA-3' and oligoB having the sequence 5'-SH-TAGCTTATCAGAC-Cy3-3') in 0.25 mM magnesium chloride solution (total volume: 1 mL) overnight at room temperature. To stabilize the solution, a mixture of 100 μM mPEG-SH and 0.5 μM mPEG-SH (MW 5000) was added for 10 min followed by the addition of 0.01% Tween 20. The functionalized nanoparticles were washed thrice with 10 mM Tris-HCl buffer (pH 8.0) containing 0.01% Tween 20 using repeated centrifugation at 12,000 rpm for 10 min. The purified nanoprobes were suspended in 1 mL of 10 mM Tris-HCl buffer (pH 8.0) containing 0.01% Tween 20 and kept at 4° C.

Figure 16A:
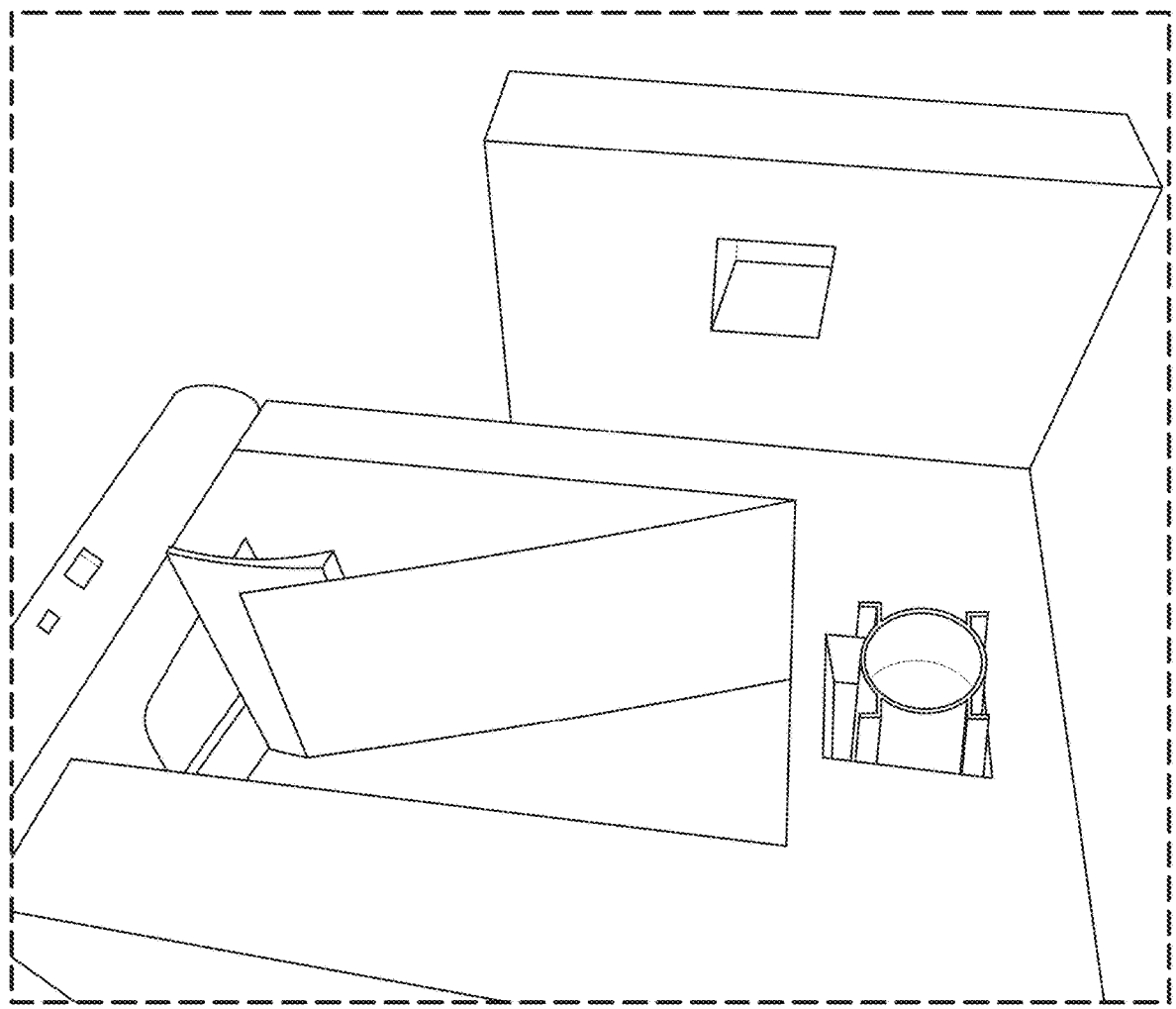
FIG. 16A is a photograph of an exemplary 3D printed mobile health electronic device accessory according to one embodiment of the present invention.
Figure 16B:
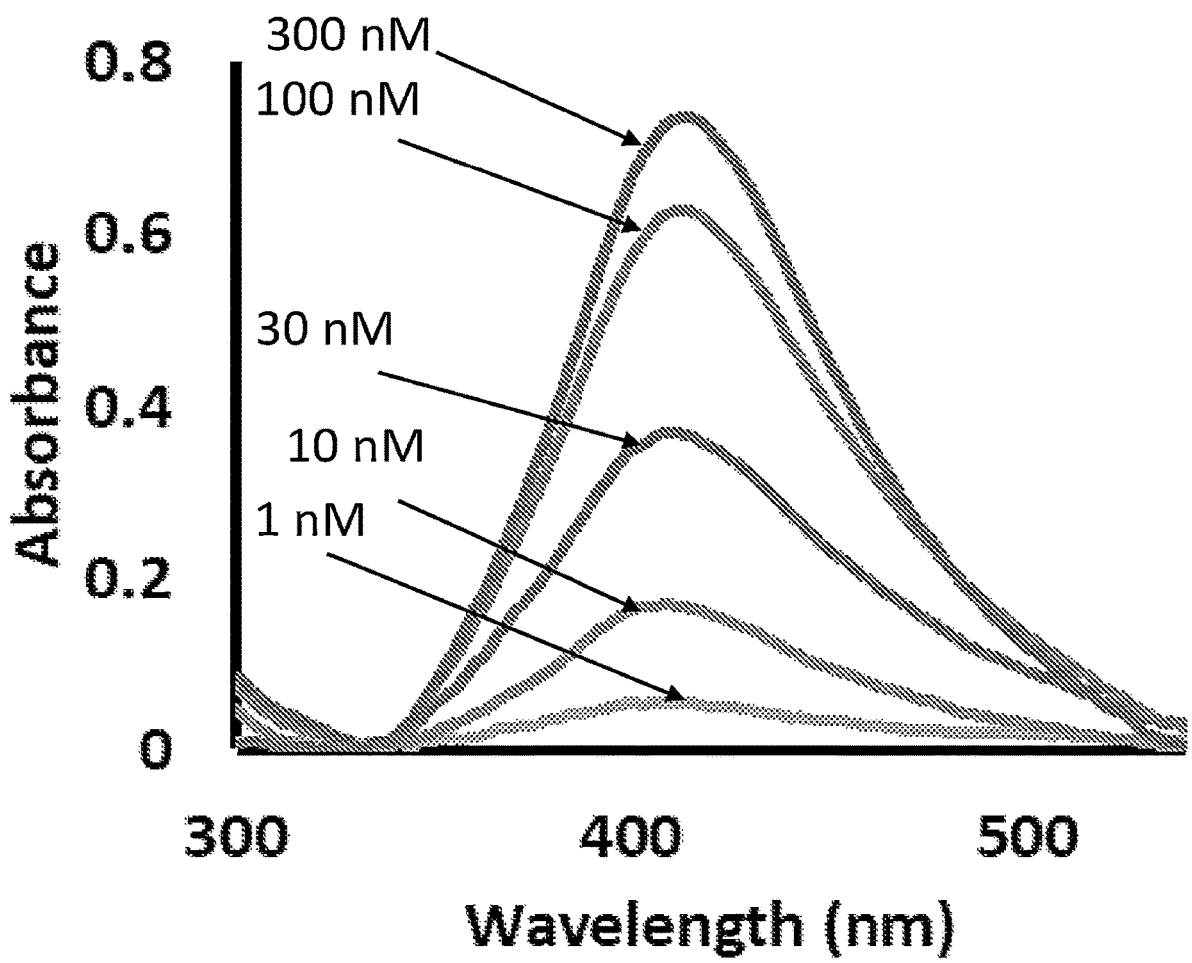
FIG. 16B illustrates an absorbance spectra of sample solutions with different microRNA-21 target concentrations.
Figure 16C:
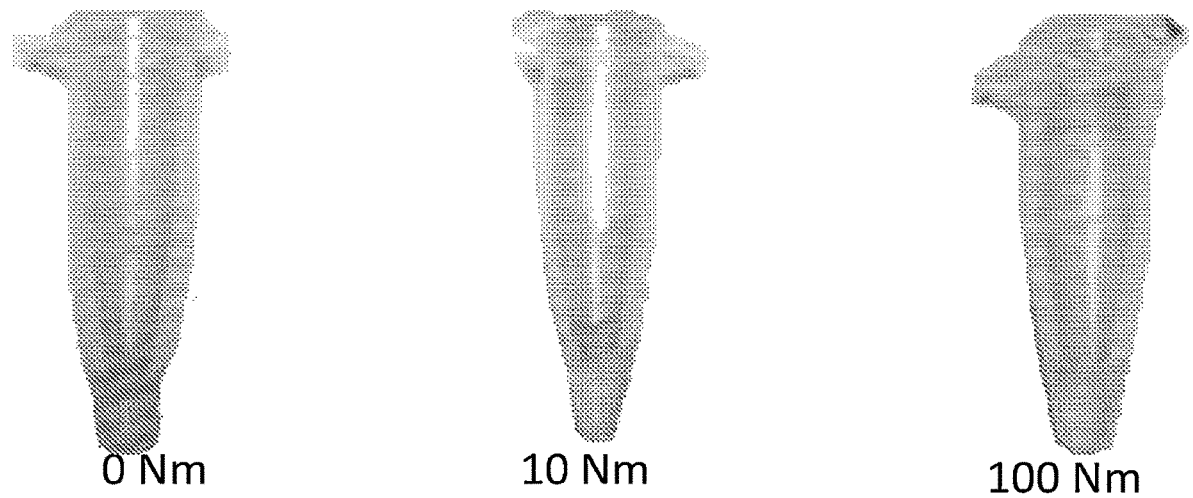
FIG. 16C is a series of photographs of exemplary sample solutions with 0 nM, 10 nM, and 100 nM of microRNA-21 target.
Figure 17:
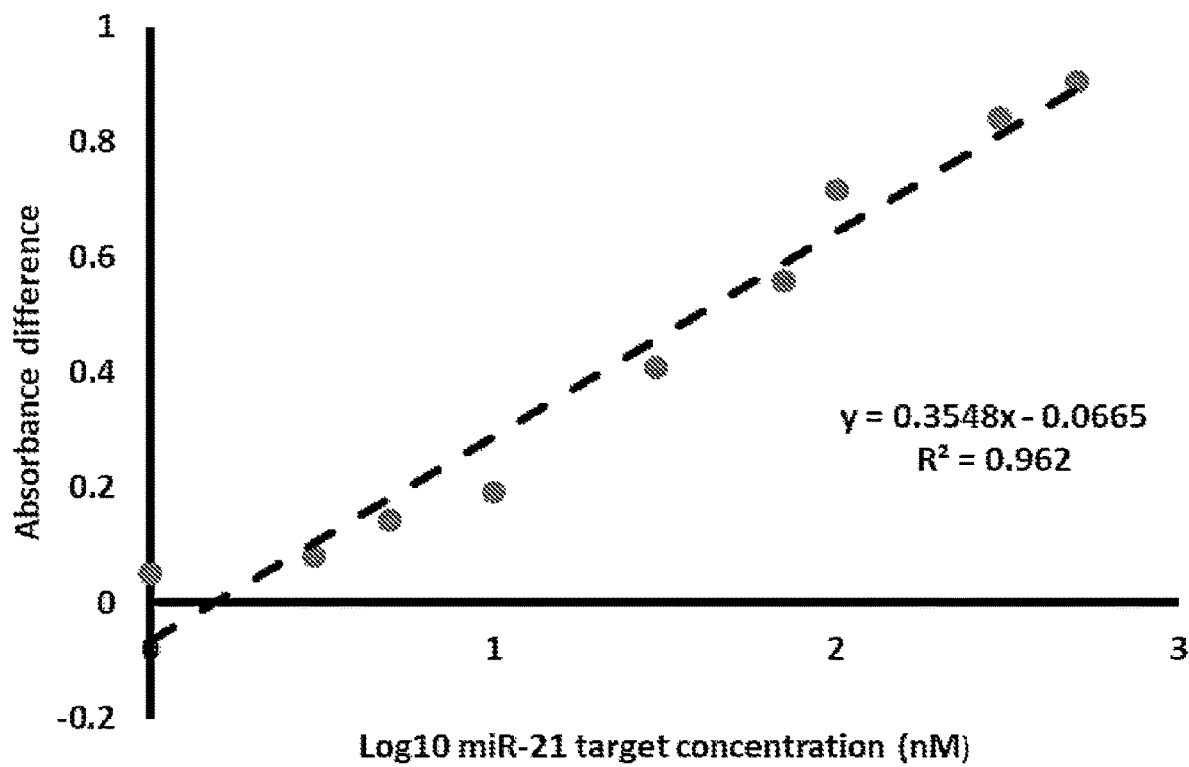
FIG. 17 is a plot showing the absorbance difference of calibration samples against LOG 10 microRNA target concentration.

To investigate the effect of miR-21 target addition on nanoprobe aggregation, samples mixed with different amounts of the miR-21 target were measured with a spectrophotometer (FLUOstar Omega, BMG LABTECH) in the UV-Vis region. The results were compared with data obtained with an exemplary Krometriks system. FIG. 16A shows the 3-D printed Krometriks accessory. In the presence of increasing miR-21 target concentrations, an increase in the absorbance of the plasmon resonance peak of isolated AgNPs at around 412 nm was observed. In addition, a decrease in the absorbance around 650 nm for aggregated AgNPs was observed (FIG. 16B for absorbance spectra). FIG. 16C shows sample solutions with 0 nM, 10 nM, and 100 nM of miR-21 target. The sample solutions turned more yellow from greyish yellow with increasing target concentration, indicating that more AgNP-nanoprobe aggregation occurred in the absence of the target miRNAs. The yellow color of the solution did not change over time indicating that the nanoprobes were well-dispersed or had properly aggregated (depending on the target amount). To quantify the colorimetric assay, the total absorbance (blank subtracted) difference was calculated by subtracting the absorbance peak intensity at 650 nm from that at 412 nm. The blank sample in this case was the solution containing only the nanoprobes AgNP-oligoA and AgNP-oligoB and no target molecules.

Figure 18:
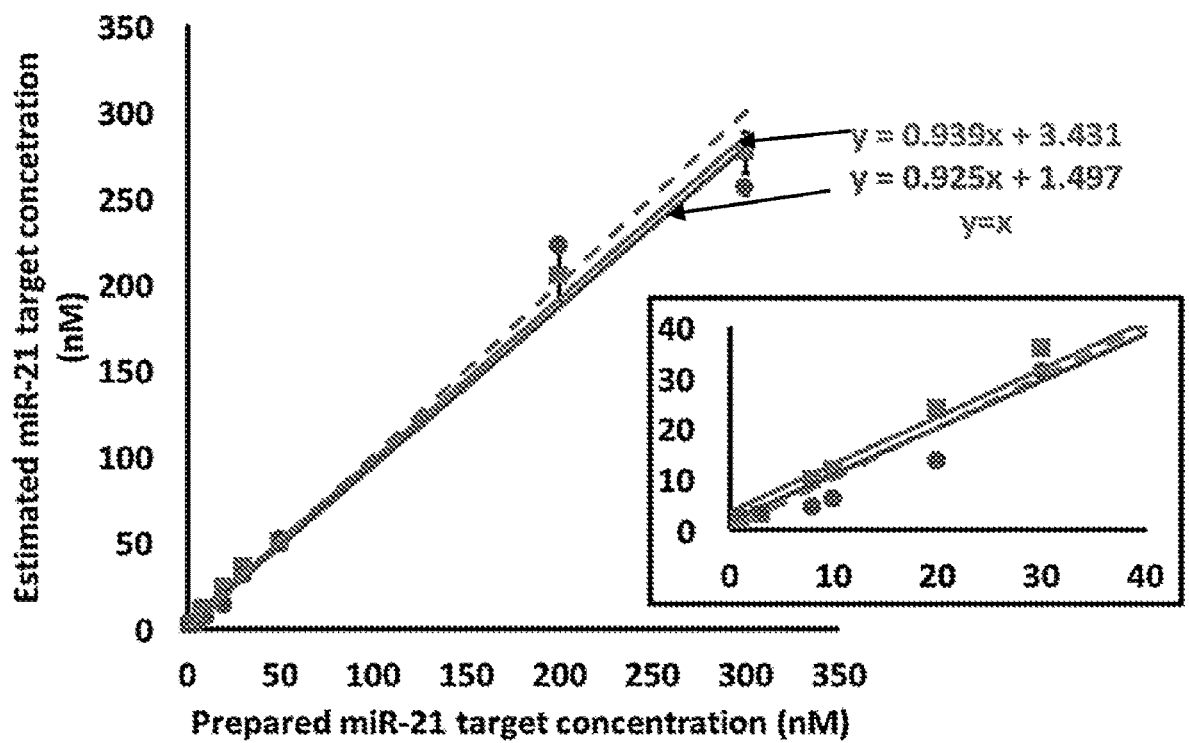
FIG. 18 is a calibration curve including estimated concentration values in comparison to prepared concentration values for different microRNA-21 target amounts.

The utility of Krometriks was demonstrated by comparing its colorimetric detection accuracy to that obtained with a benchtop spectrophotometer. First, a calibration curve was generated for both modes of measurement. The same set of calibration samples containing different miR-21 target amounts was used. For the Krometriks device, the calibration curve was generated using the process described above. For the spectrophotometer, the calculated absorbance difference (between the peak intensity at 412 nm and 650 nm) exhibited a relationship with the target concentration (on the log scale). A linear fit to the calibration data with a R2=0.962 was used as the calibration curve (FIG. 18). A set of test samples were then analyzed using the Krometriks' algorithm as well as by fitting the test data to the spectrophotometer generated calibration curve. FIG. 18 shows the estimated concentrations of the miR-21 target by the Krometriks device (line indicated by squares) and the spectrophotometer (line indicated by circles) in comparison to their prepared values. The dashed line indicates the line on which the data points should ideally lie, represented by the equation y=x. The line with a slope=0.939*0.022 and intercept=3.431*2.659 indicates the linear fit of the estimations of the Krometriks. The line with a slope=0.925*0.054 and intercept=1.497±6.654 indicates the linear fit of the estimations by the spectrophotometer. The closer the line's slope and intercept are to 1 and 0 respectively, the more accurate are the estimations. The Krometriks device provides accurate quantitative estimations, demonstrating a performance comparable to the spectrophotometer.

Figure 19:
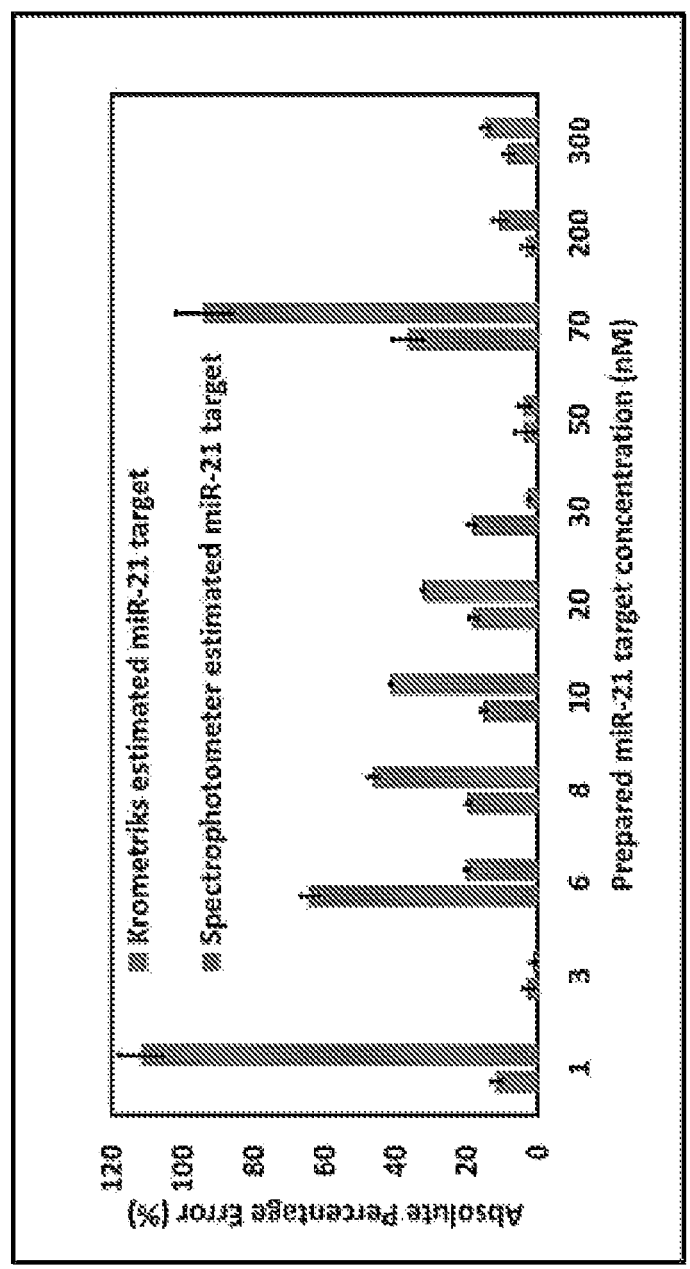
FIG. 19 is a bar plot showing the absolute percentage errors for the estimated concentration values obtained by the Krometriks app (blue) and the spectrophotometer (red) for different miR-21 target concentrations. The error bars indicate one standard deviation of variation in the measurement values.

A set of test samples was then analyzed using the Krometriks' algorithm as well as by fitting the test data to the spectrophotometer-generated calibration curve. FIG. 19 shows a bar plot of the absolute percentage error (APE) for the estimated concentrations of different miR-21 targets obtained using the Krometriks device (blue) and the spectrophotometer (red). Each APE value (calculated and discussed in the Methods section) for the Krometriks device and the spectrophotometer was an average of three measurements, respectively. The error bars indicated one standard deviation from the mean. As depicted in the plot, Krometriks provided equally good or better estimations than the spectrophotometer. To evaluate and compare the overall accuracy of the two methods, the mean absolute percentage error (MAPE) for both methods was calculated (discussed in the Methods section). The MAPE was 18.411% for Krometriks and 34.57% for the spectrophotometer. The lesser MAPE value for Krometriks concurs with the inference from the bar plot that the accuracy of Krometriks is as good or better than that of the spectrophotometer. A test of statistical significance was performed on these MAPE values based on a modified two-proportion Z-test (described in the Methods section). This gave a Z value of −0.859, indicating that the difference in the accuracy of Krometriks and the spectrophotometer was not significant (for a 5% level of significance). Therefore, the Krometriks device provided accurate quantitative estimations, demonstrating a performance comparable to the spectrophotometer. All the analyses were automated on the Krometriks app, and no additional intervention of the user was required after sample measurement to get the results. It is noteworthy that the spectrophotometer required the user's additional efforts to calculate the estimated concentrations requiring more effort and time in comparison to Krometriks. Each sample from measurement to result display, including data analysis, took less than 1 min to accomplish with Krometriks and 30 min to accomplish with the spectrophotometer. Our results showed that Krometriks could detect miR-21 targets with concentrations ranging from 1 nM to 300 nM requiring only 100 μL of solution volume. On the other hand, RT-qPCR typically requires around two to three hours for single run, laboratory-based equipment, and skilled personnel to operate sample amplification; thus, it is not suitable for use at the point-of-care setting with limited resources. The advent of more sensitive nanoparticle-based assays for miRNA detection and its integration with platforms like Krometriks holds promise for more precise and accessible diagnostics in the future.

The systems and methods described herein can be implemented in hardware, software, firmware, or combinations of hardware, software and/or firmware. In some examples, the systems and methods described in this specification may be implemented using a non-transitory computer readable medium storing computer executable instruction that when executed by one or more processors of a computer cause the computer to perform operations. Computer readable media suitable for implementing the systems and methods described in this specification include non-transitory computer-readable media, such as disk memory devices, chip memory devices, programmable logic devices, random access memory (RAM), read only memory (ROM), optical read/write memory, cache memory, magnetic read/write memory, flash memory, and application-specific integrated circuits. In addition, a computer readable medium that implements a system or method described in this specification may be located on a single device or computing platform or may be distributed across multiple devices or computing platforms.

One skilled in the art will readily appreciate that the present disclosure is well adapted to carry out the objects and obtain the ends and advantages mentioned, as well as those inherent therein. The present disclosure described herein is presently representative of preferred embodiments, are exemplary, and are not intended as limitations on the scope of the present disclosure. Changes therein and other uses will occur to those skilled in the art which are encompassed within the spirit of the present disclosure as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

REFERENCES

T. Vo-Dinh, M. Y. K. Hiromoto, G. M. Begun and R. L. Moody, "Surface-enhanced Raman spectroscopy for trace organic analysis," Anal. Chem., vol. 56, 1667, 1984

K. Kneipp, H. Kneipp, I. Itzkan, R. R Dasar, M. S. Feld, J. phys. Condens. Matter 14, R597 (2002)

Ref H.-N. Wang and T. Vo-Dinh, "Plasmonic Coupling Interference (PCI), Nanoprobes for Nucleic Acid Detection", Small, 7, 3067-3074 (2011);—Tuan Vo-Dinh and Hsin-Neng Wang "Nano-Plasmonic Molecular Probes For Plasmonics Coupling Interference", United States Patent Application 20170321280 (2017)

He, L.; Hannon, G. J. MicroRNAs: Small RNAs with a Big Role in Gene Regulation. Nat Rev Genet 2004, 5 (7), 522-531. https://doi.org/10.1038/nrg1379.

Weber, J. A.; Baxter, D. H.; Zhang, S.; Huang, D. Y.; Huang, K. H.; Lee, M. J.; Galas, D. J.; Wang, K. The MicroRNA Spectrum in 12 Body Fluids. Clin Chem 2010, 56 (11), 1733-1741. https://doi.org/10.1373/clinchem.2010.147405.

Romaine, S. P. R.; Tomaszewski, M.; Condorelli, G.; Samani, N. J. MicroRNAs in Cardiovascular Disease: An Introduction for Clinicians. Heart 2015, 101 (12), 921-928. https://doi.org/10.1136/heartjnl-2013-305402.

Verma, P.; Pandey, R. K.; Prajapati, P.; Prajapati, V. K. Circulating MicroRNAs: Potential and Emerging Biomarkers for Diagnosis of Human Infectious Diseases. Frontiers in Microbiology 2016, 7, 1274. https://doi.org/10.3389/fmicb.2016.01274.

Basak, I.; Patil, K. S.; Alves, G.; Larsen, J. P.; Møller, S. G. MicroRNAs as Neuroregulators, Biomarkers and Therapeutic Agents in Neurodegenerative Diseases. Cell Mol Life Sci 2016, 73 (4), 811-827. https://doi.org/10.1007/s00018-015-2093-x.

Guay, C.; Regazzi, R. Circulating MicroRNAs as Novel Biomarkers for Diabetes Mellitus. Nat Rev Endocrinol 2013, 9 (9), 513-521. https://doi.org/10.1038/nrendo.2013.86.

Hicks, S. D.; Middleton, F. A. A Comparative Review of MicroRNA Expression Patterns in Autism Spectrum Disorder. Frontiers in Psychiatry 2016, 7, 176. https://doi.org/10.3389/fpsyt.2016.00176.

Redell, J. B.; Moore, A. N.; Ward, N. H.; Hergenroeder, G. W.; Dash, P. K. Human Traumatic Brain Injury Alters Plasma MicroRNA Levels. J Neurotrauma 2010, 27 (12), 2147-2156. https://doi.org/10.1089/neu.2010.1481.

Mouillet-Richard, S.; Baudry, A.; Launay, J.-M.; Kellermann, O. MicroRNAs and Depression. Neurobiol Dis 2012, 46 (2), 272-278. https://doi.org/10.1016/j.nbd.2011.12.035.

Reid, G.; Kirschner, M. B.; van Zandwijk, N. Circulating MicroRNAs: Association with Disease and Potential Use as Biomarkers. Crit Rev Oncol Hematol 2011, 80 (2), 193-208. https://doi.org/10.1016/j.critrevonc.2010.11.004.

Weiland, M.; Gao, X.-H.; Zhou, L.; Mi, Q.-S. Small RNAs Have a Large Impact: Circulating MicroRNAs as Biomarkers for Human Diseases. RNA Biol 2012, 9 (6), 850-859. https://doi.org/10.4161/rna.20378.

Hayes, J.; Peruzzi, P. P.; Lawler, S. MicroRNAs in Cancer: Biomarkers, Functions and Therapy. Trends Mol Med 2014, 20 (8), 460-469. https://doi.org/10.1016/j.molmed.2014.06.005.

Iorio, M. V.; Croce, C. M. MicroRNA Dysregulation in Cancer: Diagnostics, Monitoring and Therapeutics. A Comprehensive Review. EMBO Mol Med 2012, 4 (3), 143-159. https://doi.org/10.1002/emmm.201100209.

Lu, J.; Getz, G.; Miska, E. A.; Alvarez-Saavedra, E.; Lamb, J.; Peck, D.; Sweet-Cordero, A.; Ebert, B. L.; Mak, R. H.; Ferrando, A. A.; Downing, J. R.; Jacks, T.; Horvitz, H. R.; Golub, T. R. MicroRNA Expression Profiles Classify Human Cancers. Nature 2005, 435 (7043), 834-838. https://doi.org/10.1038/nature03702.

Johnson, B. N.; Mutharasan, R. Biosensor-Based MicroRNA Detection: Techniques, Design, Performance, and Challenges. Analyst 2014, 139 (7), 1576-1588. https://doi.org/10.1039/C3AN01677C.

Kilic, T.; Erdem, A.; Ozsoz, M.; Carrara, S. MicroRNA Biosensors: Opportunities and Challenges among Conventional and Commercially Available Techniques. Biosens Bioelectron 2018, 99, 525-546. https://doi.org/10.1016/j.bios.2017.08.007.

Degliangeli, F.; Pompa, P. P.; Fiammengo, R. Nanotechnology-Based Strategies for the Detection and Quantification of MicroRNA. Chemistry—A European Journal 2014, 20 (31), 9476-9492. https://doi.org/I0.1002/chem.201402649.

Tian, T.; Wang, J.; Zhou, X. A Review: MicroRNA Detection Methods. Org Biomol Chem 2015, 13 (8), 2226-2238. https://doi.org/10.1039/c4ob02104e.

Sabela, M.; Balme, S.; Bechelany, M.; Janot, J.-M.; Bisetty, K. A Review of Gold and Silver Nanoparticle-Based Colorimetric Sensing Assays. Advanced Engineering Materials 2017, 19 (12), 1700270. https://doi.org/10.1002/adem.201700270.

Doria, G.; Conde, J.; Veigas, B.; Giestas, L.; Almeida, C.; Assunção, M.; Rosa, J.; Baptista, P. V. Noble Metal Nanoparticles for Biosensing Applications. Sensors (Basel) 2012, 12 (2), 1657-1687. https://doi.org/10.3390/s120201657.

Wang, W.; Kong, T.; Zhang, D.; Zhang, J.; Cheng, G. Label-Free MicroRNA Detection Based on Fluorescence Quenching of Gold Nanoparticles with a Competitive Hybridization. Anal. Chem. 2015, 87 (21), 10822-10829. https://doi.org/I0.1021/acs.analchem.5b01930.

Miao, J.; Wang, J.; Guo, J.; Gao, H.; Han, K.; Jiang, C.; Miao, P. A Plasmonic Colorimetric Strategy for Visual MiRNA Detection Based on Hybridization Chain Reaction. Sci Rep 2016, 6 (1), 32219. https://doi.org/10.1038/srep32219.

Kwon, L.; Long, K. D.; Wan, Y.; Yu, H.; Cunningham, B. T. Medical Diagnostics with Mobile Devices: Comparison of Intrinsic and Extrinsic Sensing. Biotechnol Adv 2016, 34 (3), 291-304. https://doi.org/10.1016/j.biotechadv.2016.02.010.

Roda, A.; Michelini, E.; Zangheri, M.; Fusco, M. D.; Calabria, D.; Simoni, P. Smartphone-Based Biosensors: A Critical Review and Perspectives. TrAC Trends in Analytical Chemistry 2016, C (79), 317-325. https://doi.org/10.1016/j.trac.2015.10.019.

Zhang, D.; Liu, Q. Biosensors and Bioelectronics on Smartphone for Portable Biochemical Detection. Biosens Bioelectron 2016, 75, 273-284. https://doi.org/10.1016/j.bios.2015.08.037.

Kanchi, S.; Sabela, M. I.; Mdluli, P. S.; Inamuddin; Bisetty, K. Smartphone Based Bioanalytical and Diagnosis Applications: A Review. Biosens Bioelectron 2018, 102, 136-149. https://doi.org/10.1016/j.bios.2017.11.021.

Nie, H.; Wang, W.; Li, W.; Nie, Z.; Yao, S. A Colorimetric and Smartphone Readable Method for Uracil-DNA Glycosylase Detection Based on the Target-Triggered Formation of G-Quadruplex. Analyst 2015, 140 (8), 2771-2777. https://doi.org/10.1039/c4an02339k.

Chen, Y.; Fu, Q.; Li, D.; Xie, J.; Ke, D.; Song, Q.; Tang, Y.; Wang, H. A Smartphone Colorimetric Reader Integrated with an Ambient Light Sensor and a 3D Printed Attachment for On-Site Detection of Zearalenone. Anal Bioanal Chem 2017, 409 (28), 6567-6574. https://doi.org/10.1007/s00216-017-0605-2.

Lopez-Ruiz, N.; Curto, V. F.; Erenas, M. M.; Benito-Lopez, F.; Diamond, D.; Palma, A. J.; Capitan-Vallvey, L. F. Smartphone-Based Simultaneous PH and Nitrite Colorimetric Determination for Paper Microfluidic Devices. Anal Chem 2014, 86 (19), 9554-9562. https://doi.org/10.1021/ac5019205.

Oncescu, V.; O'Dell, D.; Erickson, D. Smartphone Based Health Accessory for Colorimetric Detection of Biomarkers in Sweat and Saliva. Lab Chip 2013, 13 (16), 3232-3238. https://doi.org/10.1039/c31c50431j.

Kim, S. C.; Jalal, U. M.; Im, S. B.; Ko, S.; Shim, J. S. A Smartphone-Based Optical Platform for Colorimetric Analysis of Microfluidic Device. Sensors and Actuators B: Chemical 2017, C (239), 52-59. https://doi.org/10.1016/j.snb.2016.07.159.

Chan, H. N.; Shu, Y.; Xiong, B.; Chen, Y.; Chen, Y.; Tian, Q.; Michael, S. A.; Shen, B.; Wu, H. Simple, Cost-Effective 3D Printed Microfluidic Components for Disposable, Point-of-Care Colorimetric Analysis. ACS Sens. 2016, 1 (3), 227-234. https://doi.org/10.1021/acssensors.5b00100.

Lee, S.; Oncescu, V.; Mancuso, M.; Mehta, S.; Erickson, D. A Smartphone Platform for the Quantification of Vitamin D Levels. Lab Chip 2014, 14 (8), 1437-1442. https://doi.org/10.1039/c31c51375k.

Oncescu, V.; Mancuso, M.; Erickson, D. Cholesterol Testing on a Smartphone. Lab Chip 2014, 14 (4), 759-763. https://doi.org/10.1039/C3LC51194D.

Choi, S.; Kim, S.; Yang, J.-S.; Lee, J.-H.; Joo, C.; Jung, H.-I. Real-Time Measurement of Human Salivary Cortisol for the Assessment of Psychological Stress Using a Smartphone. Sensing and Bio-Sensing Research 2014, 2, 8-11. https://doi.org/10.1016/j.sbsr.2014.08.001.

Jung, Y.; Kim, J.; Awofeso, O.; Kim, H.; Regnier, F.; Bae, E. Smartphone-Based Colorimetric Analysis for Detection of Saliva Alcohol Concentration. Appl Opt 2015, 54 (31), 9183-9189. https://doi.org/10.1364/AO.54.009183.

Wang, F.; Lu, Y.; Yang, J.; Chen, Y.; Jing, W.; He, L.; Liu, Y. A Smartphone Readable Colorimetric Sensing Platform for Rapid Multiple Protein Detection. Analyst 2017, 142 (17), 3177-3182. https://doi.org/10.1039/C7AN00990A.

Priye, A.; Wong, S.; Bi, Y.; Carpio, M.; Chang, J.; Coen, M.; Cope, D.; Harris, J.; Johnson, J.; Keller, A.; Lim, R.; Lu, S.; Millard, A.; Pangelinan, A.; Patel, N.; Smith, L.; Chan, K.; Ugaz, V. M. Lab-on-a-Drone: Toward Pinpoint Deployment of Smartphone-Enabled Nucleic Acid-Based Diagnostics for Mobile Health Care. Anal. Chem. 2016, 88 (9), 4651-4660. https://doi.org/10.1021/acs.analchem.5b04153.

Mancuso, M.; Cesarman, E.; Erickson, D. Detection of Kaposi's Sarcoma Associated Herpesvirus Nucleic Acids Using a Smartphone Accessory. Lab Chip 2014, 14 (19), 3809-3816. https://doi.org/10.1039/C4LC00517A.

Wang, H.-N.; Vo-Dinh, T. Plasmonic Coupling Interference (PCI) Nanoprobes for Nucleic Acid Detection. Small 2011, 7 (21), 3067-3074. https://doi.org/10.1002/smll.201101380.

Wang, H.-N.; Crawford, B. M.; Norton, S. J.; Vo-Dinh, T. Direct and Label-Free Detection of MicroRNA Cancer Biomarkers Using SERS-Based Plasmonic Coupling Interference (PCI) Nanoprobes. J. Phys. Chem. B 2019, 123 (48), 10245-10251. https://doi.org/10.1021/acs.jpcb.9b06804.

Jain, P. K.; El-Sayed, M. A. Plasmonic Coupling in Noble Metal Nanostructures. Chemical Physics Letters 2010, 487 (4), 153-164. https://doi.org/10.1016/j.cplett.2010.01.062.

Duan, J.; Yin, H.; Wei, R.; Wang, W. Facile Colorimetric Detection of Hg2+ Based on Anti-Aggregation of Silver Nanoparticles. Biosens Bioelectron 2014, 57, 139-142. https://doi.org/10.1016/j.bios.2014.02.007.

Liu, Y.; Zhang, L.; Wei, W.; Zhao, H.; Zhou, Z.; Zhang, Y.; Liu, S. Colorimetric Detection of Influenza A Virus Using Antibody-Functionalized Gold Nanoparticles. Analyst 2015, 140 (12), 3989-3995. https://doi.org/10.1039/C5AN00407A.

Krichevsky, A. M.; Gabriely, G. MiR-21: A Small Multi-Faceted RNA. J Cell Mol Med 2009, 13 (1), 39-53. https://doi.org/10.1111/j.1582-4934.2008.00556.x.

Selcuklu, S. D.; Donoghue, M. T. A.; Spillane, C. MiR-21 as a Key Regulator of Oncogenic Processes. Biochem Soc Trans 2009, 37 (Pt 4), 918-925. https://doi.org/10.1042/BST0370918.

Wu, Y. E.; Parikshak, N. N.; Belgard, T. G.; Geschwind, D. H. Genome-Wide, Integrative Analysis Implicates MicroRNA Dysregulation in Autism Spectrum Disorder. Nat Neurosci 2016, 19 (11), 1463-1476. https://doi.org/10.1038/nn.4373.

Ebner, M. Color Constancy; John Wiley & Sons, 2007.

Hunt, R. W. G.; Pointer, M. R. Measuring Colour, John Wiley & Sons, 2011.

Yetisen, A. K.; Martinez-Hurtado, J. L.; Garcia-Melendrez, A.; Vasconcellos, F. da C.; Lowe, C. R. A Smartphone Algorithm with Inter-Phone Repeatability for the Analysis of Colorimetric Tests. Sensors and Actuators B: Chemical 2014, C (196), 156-160. https://doi.org/10.1016/j.snb.2014.01.077.

Hong, J. I.; Chang, B.-Y. Development of the Smartphone-Based Colorimetry for Multi-Analyte Sensing Arrays. Lab Chip 2014, 14 (10), 1725-1732. https://doi.org/10.1039/c3lc51451j.

Vashist, S. K.; van Oordt, T.; Schneider, E. M.; Zengerle, R.; von Stetten, F.; Luong, J. H. T. A Smartphone-Based Colorimetric Reader for Bioanalytical Applications Using the Screen-Based Bottom Illumination Provided by Gadgets. Biosens Bioelectron 2015, 67, 248-255. https://doi.org/10.1016/j.bios.2014.08.027.

Dutta, S.; Saikia, G. P.; Sarma, D. J.; Gupta, K.; Das, P.; Nath, P. Protein, Enzyme and Carbohydrate Quantification Using Smartphone through Colorimetric Digitization Technique. J Biophotonics 2017, 10 (5), 623-633. https://doi.org/10.1002/jbio.201500329.

Su, K.; Zou, Q.; Hu, N.; Wang, P. High-Sensitive and High-Efficient Biochemical Analysis Method Using a Bionic Electronic Eye in Combination with a Smartphone-Based Colorimetric Reader System. Annu Int Conf IEEE Eng Med Biol Soc 2015, 2015, 7720-7723. https://doi.org/10.1109/EMBC.2015.7320181.

Wang, J.-W.; Czech, B.; Weigel, D. MiR156-Regulated SPL Transcription Factors Define an Endogenous Flowering Pathway in *Arabidopsis Thaliana*. Cell 2009, 138 (4), 738-749. https://doi.org/10.1016/j.cell.2009.06.014.

Crawford, B. M.; Strobbia, P.; Wang, H.-N.; Zentella, R.; Boyanov, M. I.; Pei, Z.-M.; Sun, T.-P.; Kemner, K. M.; Vo-Dinh, T. Plasmonic Nanoprobes for in Vivo Multimodal Sensing and Bioimaging of MicroRNA within Plants. ACS Appl. Mater. Interfaces 2019, 11 (8), 7743-7754. https://doi.org/10.1021/acsami.8b19977.

Wang, H. N., & Vo-Dinh, T. (2011). Plasmonic coupling interference (PCI) nanoprobes for nucleic acid detection. Small, 7(21), 3067-3074. doi:10.1002/smll.201101380

Hernandez-Neuta, I., Neumann, F., Brightmeyer, J., Ba Tis, T., Madaboosi, N., Wei, Q., Nilsson, M. (2019). Smartphone-based clinical diagnostics: towards democratization of evidence-based health care. J Intern Med, 285(1), 19-39. doi:10.1111/joim.12820

Kwon, L., Long, K. D., Wan, Y., Yu, H., & Cunningham, B. T. (2016). Medical diagnostics with mobile devices: Comparison of intrinsic and extrinsic sensing. Biotechnol Adv, 34(3), 291-304. doi:10.1016/j.biotechadv.2016.02.010

Johnson, R. A.; Miller, I.; Freund, J. E. *Miller & Freund's Probability and Statistics for Engineers,* 9th edition; Pearson: Boston, MA, USA, 2016.

What is claimed is:

1. A diagnostic mobile health system for detecting biomarkers, the system comprising:
   an electronic device including an image sensor configured to capture image data;
   a sample housing configured to removably attach to the electronic device,
      wherein the sample housing includes a slot to receive a sample container that contains a sample,
      wherein the sample container received in the slot is positioned to allow the image sensor of the electronic device to capture image data for the sample when the sample housing is attached to the electronic device; and
   a computing device including at least one processor configured for:
      receiving, from the electronic device, image data for the sample that is captured by the image sensor of the electronic device when the sample container containing the sample is received by the sample housing attached to the electronic device; and
      detecting at least one biomarker for the sample based on the received image data.

2. The system of claim 1, wherein the sample housing further includes a diffuser plate that includes an opaque component and a translucent component.

3. The system of claim 1, wherein an interior surface of the sample housing opposite the image sensor of the electronic device includes a background component.

4. The system of claim 1, wherein the sample housing includes a cover positioned on a top side of the sample housing to block external light from entering the sample housing.

5. The system of claim 1, wherein the at least one biomarker includes microRNA.

6. The system of claim 1, wherein the at least one processor of the computing device is further configured for:
analyzing a region of interest within the received image data;
determining a red, green blue (RGB) value for each pixel within the region of interest;
normalizing the RGB values in comparison to RGB data for template region of interest;
converting the normalized RGB values to tristimulus values; and
converting the tristimulus values to CIELAB values.

7. The system of claim 1, wherein the processor of the computing device is further operable to detect the at least one biomarker using at least one of Raman scattering, luminescence detection, fluorescence detection, and/or phosphorescence detection.

8. The system of claim 1, wherein the sample includes a nanoparticle assay, wherein the processor of the computing device is operable to quantify the at least one biomarker based on a color change of the sample using the received image data.

9. A method of biomarker detection comprising:
receiving a sample via a sample housing removably attached to an electronic device;
illuminating the sample with at least one light source of the electronic device;
capturing image data of the sample via an image sensor of the electronic device, wherein the image data includes a red, green, and blue (RGB) value for each pixel of the captured image data;
transmitting the captured image data to a computing device including a processor;
averaging the RGB values using the processor of the computing device;
normalizing the RGB values in comparison to RGB data for a template region of interest using the processor of the computing device;
converting the normalized RGB values to color data and concentration data using the processor of the computing device; and
detecting at least one biomarker for the sample based on the color data and the concentration data using the processor of the computing device.

10. The method of claim 9, wherein the sample housing further includes a diffuser plate that includes an opaque component and a translucent component.

11. The method of claim 9, wherein the sample housing includes a cover positioned on a top side of the sample housing to block external light from entering the sample housing.

12. The method of claim 9, wherein the at least one biomarker includes microRNA.

13. The method of claim 9, further comprising detecting the at least one biomarker using at least one of Raman scattering, luminescence detection, fluorescence detection, and/or phosphorescence detection.

14. The method of claim 9, further comprising, using the processor of the computing device, quantifying the at least one biomarker based on a color change of the sample, wherein the sample includes a nanoparticle assay.

15. A mobile health device for detecting biomarkers comprising:
a sample housing including at least one slot, a cover, and a back plate that is removably attached to the mobile health device;
an imaging sensor, and
at least one processor;
wherein the at least one slot is operable to receive a sample container that contains a sample;
wherein the sample container received in the at least one slot is positioned to allow the image sensor to capture image data for the sample when the sample housing is attached to the mobile health device;
wherein the cover is positioned on a top side of the sample housing to block external light from entering the sample housing; and
wherein the at least one processor is configured for:
receiving, from the image sensor, image data for the sample that is captured by the image sensor when the sample container containing the sample is received by the sample housing attached to mobile health device; and
detecting at least one biomarker for the sample based on the received based on the image data.

16. The device of claim 15, wherein the at least one biomarker includes microRNA.

17. The device of claim 15, the at least one processor further configured for:
analyzing a region of interest within the received image data;
determining a red, green, blue (RGB) value for each pixel within the region of interest;
normalizing the RGB values in comparison to RGB data for a template region of interest;
converting the normalized RGB values to tristimulus values; and
converting the tristimulus values to CIELAB values.

18. The device of claim 15, wherein the at least one processor is further operable to detect the at least one biomarker using at least one of Raman scattering, luminescence detection, fluorescence detection, and/or phosphorescence detection.

19. The device of claim 15, wherein the sample includes a nanoparticle assay, wherein the at least one processor is operable to quantify the at least one biomarker based on a color change of the sample using the received image data.

* * * * *